US010166395B2

(12) United States Patent
Tracey et al.

(10) Patent No.: US 10,166,395 B2
(45) Date of Patent: Jan. 1, 2019

(54) INHIBITION OF INFLAMMATORY CYTOKINE PRODUCTION BY CHOLINERGIC AGONISTS AND VAGUS NERVE STIMULATION

(71) Applicant: The Feinstein Institute for Medical Research, Great Neck, NY (US)

(72) Inventors: Kevin J. Tracey, Old Greenwich, CT (US); Jared M. Huston, New York, NY (US)

(73) Assignee: The Feinstein Institute for Medical Research, Great Neck, NY (US)

( * ) Notice: Subject to any disclaimer, the term of this patent is extended or adjusted under 35 U.S.C. 154(b) by 0 days.

(21) Appl. No.: 14/569,504

(22) Filed: Dec. 12, 2014

(65) Prior Publication Data
US 2015/0100100 A1    Apr. 9, 2015

Related U.S. Application Data

(63) Continuation of application No. 10/990,938, filed on Nov. 17, 2004, now Pat. No. 8,914,114, which is a continuation-in-part of application No. 10/446,625, filed on May 28, 2003, now Pat. No. 6,838,471, which is a continuation of application No. 09/855,446, filed on May 15, 2001, now Pat. No. 6,610,713.

(60) Provisional application No. 60/206,364, filed on May 23, 2000.

(51) Int. Cl.
*A61K 31/44*   (2006.01)
*A61N 1/36*    (2006.01)

(52) U.S. Cl.
CPC .......... *A61N 1/36167* (2013.01); *A61K 31/44* (2013.01); *A61N 1/3606* (2013.01); *A61N 1/36053* (2013.01); *Y02A 50/385* (2018.01); *Y02A 50/411* (2018.01)

(58) Field of Classification Search
None
See application file for complete search history.

(56) References Cited

U.S. PATENT DOCUMENTS

| | | |
|---|---|---|
| 2,164,121 A | 6/1939 | Pescador |
| 3,363,623 A | 1/1968 | Atwell |
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor et al. |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |

(Continued)

FOREIGN PATENT DOCUMENTS

| DE | 2628045 A1 | 1/1977 |
|---|---|---|
| DE | 3736664 A1 | 5/1989 |

(Continued)

OTHER PUBLICATIONS

US 6,184,239, 02/2001, Puskas (withdrawn)
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Peuker; The nerve supply of the human auricle; Clin. Anat.; 15(1); pp. 35-37; Jan. 2002.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.
Stevens et al.; The anti-inflammatory effect of some immunosuppressive agents; J. Path.; 97(2); pp. 367-373; 1969 (year of pub. sufficiently earlier than effective US filed and any foreign priority date).

(Continued)

*Primary Examiner* — Celeste A Roney
(74) *Attorney, Agent, or Firm* — Shay Glenn LLP

(57) ABSTRACT

A method of inhibiting the release of a proinflammatory cytokine in a cell is disclosed. The method comprises treating the cell with a cholinergic agonist. The method is useful in patients at risk for, or suffering from, a condition mediated by an inflammatory cytokine cascade, for example endotoxic shock. The cholinergic agonist treatment can be effected by stimulation of an efferent vagus nerve fiber, or the entire vagus nerve.

20 Claims, 17 Drawing Sheets

(56) References Cited

U.S. PATENT DOCUMENTS

| | | | |
|---|---|---|---|
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold et al. |
| 5,567,724 A | 10/1996 | Kelleher et al. |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A * | 12/1997 | Zabara ............... A61N 1/3621 |
| | | | 607/118 |
| 5,705,337 A | 1/1998 | Gold et al. |
| 5,707,400 A | 1/1998 | Terry, Jr. et al. |
| 5,709,853 A | 1/1998 | Lino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A * | 6/1999 | Taylor ............... A61B 17/122 |
| | | | 128/898 |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A * | 8/2000 | Naritoku ............ A61N 1/36082 |
| | | | 607/45 |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osorio et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |

(56) References Cited

U.S. PATENT DOCUMENTS

| | | |
|---|---|---|
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,544,497 B2 | 6/2009 | Sinclair et al. |
| 7,711,432 B2 | 5/2010 | Thimineur et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,937,145 B2 | 5/2011 | Dobak |
| 8,391,970 B2 | 3/2013 | Tracey et al. |
| 8,412,338 B2 | 4/2013 | Faltys |
| 8,612,002 B2 | 12/2013 | Faltys et al. |
| 8,729,129 B2 | 5/2014 | Tracey et al. |
| 8,788,034 B2 | 7/2014 | Levine et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 2001/0002441 A1 | 5/2001 | Boveja |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubtich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0283198 A1 | 12/2005 | Haubrich et al. |
| 2006/0009815 A1 | 1/2006 | Boveja et al. |

(56) References Cited

U.S. PATENT DOCUMENTS

| | | |
|---|---|---|
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Ben-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0129200 A1 | 6/2006 | Kurokawa |
| 2006/0142822 A1 | 6/2006 | Tulgar |
| 2006/0155495 A1 | 7/2006 | Osorio et al. |
| 2006/0161216 A1 | 7/2006 | John et al. |
| 2006/0167498 A1 | 7/2006 | DiLorenzo |
| 2006/0173508 A1 | 8/2006 | Stone et al. |
| 2006/0178691 A1 | 8/2006 | Binmoeller |
| 2006/0178703 A1* | 8/2006 | Huston ............ A61N 1/36053 607/2 |
| 2006/0206155 A1 | 9/2006 | Ben-David et al. |
| 2006/0259077 A1 | 11/2006 | Pardo et al. |
| 2006/0271115 A1 | 11/2006 | Ben-Ezra et al. |
| 2006/0287678 A1 | 12/2006 | Shafer |
| 2006/0287679 A1 | 12/2006 | Stone |
| 2006/0293723 A1 | 12/2006 | Whitehurst et al. |
| 2007/0055324 A1 | 3/2007 | Thompson et al. |
| 2007/0067004 A1 | 3/2007 | Boveja et al. |
| 2007/0093434 A1 | 4/2007 | Rossetti et al. |
| 2007/0100380 A1 | 5/2007 | Fukui |
| 2007/0118178 A1 | 5/2007 | Fukui |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0150021 A1 | 6/2007 | Chen et al. |
| 2007/0244522 A1 | 10/2007 | Overstreet |
| 2008/0140138 A1 | 6/2008 | Ivanova et al. |
| 2008/0208266 A1 | 8/2008 | Lesser et al. |
| 2008/0234790 A1 | 9/2008 | Bayer et al. |
| 2008/0249439 A1 | 10/2008 | Tracey et al. |
| 2009/0143831 A1 | 6/2009 | Huston et al. |
| 2009/0247934 A1 | 10/2009 | Tracey et al. |
| 2009/0248097 A1 | 10/2009 | Tracey et al. |
| 2009/0275997 A1 | 11/2009 | Faltys et al. |
| 2010/0241183 A1 | 9/2010 | DiLorenzo |
| 2010/0249859 A1 | 9/2010 | DiLorenzo |
| 2011/0054569 A1 | 3/2011 | Zitnik et al. |
| 2011/0106208 A1 | 5/2011 | Faltys et al. |
| 2011/0224749 A1 | 9/2011 | Ben-David et al. |
| 2013/0079834 A1 | 3/2013 | Levine |
| 2013/0253413 A1 | 9/2013 | Levine et al. |
| 2014/0330349 A1 | 11/2014 | Levine et al. |
| 2015/0057722 A1 | 2/2015 | Faltys et al. |
| 2015/0066123 A1 | 3/2015 | Faltys et al. |
| 2016/0038745 A1 | 2/2016 | Faltys et al. |
| 2016/0051813 A1 | 2/2016 | Faltys et al. |
| 2016/0067497 A1 | 3/2016 | Levine et al. |
| 2016/0096016 A1 | 4/2016 | Tracey et al. |
| 2016/0096017 A1 | 4/2016 | Levine et al. |
| 2016/0114165 A1 | 4/2016 | Levine et al. |
| 2017/0113044 A1 | 4/2017 | Levine et al. |
| 2017/0266448 A1 | 9/2017 | Tracey et al. |
| 2017/0304613 A1 | 10/2017 | Faltys et al. |
| 2018/0001096 A1 | 1/2018 | Faltys et al. |
| 2018/0021217 A1 | 1/2018 | Tracey et al. |

FOREIGN PATENT DOCUMENTS

| | | |
|---|---|---|
| DE | 20316509 U1 | 4/2004 |
| EP | 0438510 B1 | 8/1996 |
| EP | 0726791 B1 | 6/2000 |
| EP | 1001827 B1 | 1/2004 |
| GB | 04133 | 2/1910 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO2003/072135 A2 | 9/2003 |
| WO | WO2004/000413 A2 | 12/2003 |
| WO | WO2004/064918 A1 | 8/2004 |

OTHER PUBLICATIONS

Tekdemir et al.; A clinico-anatomic study of the auricular branch of the vagus nerve and arnold's ear-cough reflex; Surg. Radiol. Anat.; 20(4); pp. 253-257; Mar. 1998.

Zamotrinsky et al.; Vagal neurostimulation in patients with coronary artery disease; Auton. Neurosci.; 88(1-2); pp. 109-116; Apr. 2001.

Zitnik et al.; U.S. Appl. No. 14/630,613 entitled "Vagus nerve stimulation screening test," filed Feb. 24, 2015.

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, No. 1, pp. 32-41, Jan. 1, 1999.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract only).

Beliavskaia et al.,"On the effects of prolonged stimulation of the peripheral segment of the vagus nerve . . . ," Fiziologicheskii Zhurnal SSSR Imeni I.M. Sechenova., vol. 52(11); p. 1315-1321, Nov. 1966.

Ben-Noun et al.; Neck circumference as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al., Vagus nerve stimulation attenuates cardiac TNF production in endotoxic shock, (supplemental to SHOCK, vol. 15, 2001, Injury, inflammation and sepsis: laboratory and clinical approaches, SHOCK, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression IN shock, New York Surgical Society, New York, NY, Apr. 11, 2001.

Bernik, et al., Pharmacological stimulation of the cholinergic anti-inflammatory pathway, The Journal of Experimental Medicine, vol. 195, No. 6, pp. 781-788, Mar. 18, 2002.

(56) References Cited

OTHER PUBLICATIONS

Besedovsky, H., et al., Immunoregulatory feedback between interleukin-1 and glucocorticoid hormones, Science, vol. 233, No. 4764, pp. 652-654, Aug. 1986.
Bhattacharya, S.K. et al., Central muscarinic receptor subtypes and carrageenin-induced paw oedema in rats, Res. Esp. Med. vol. 191(1), pp. 65-76, Dec. 1991.
Bianchi et al., Suppression of proinflammatory cytokines in monocytes by a tetravalent guanylhydrazone, Journal of Experimental Medicine, vol. 183, pp. 927-936, Mar. 1996.
Blackwell, T. S. et al., Sepsis and cytokines: current status, Br. J. Anaesth., vol. 77(1), pp. 110-117, Jul. 1996.
Blum, A. et al., Role of cytokines in heart failure, Am. Heart J., vol. 135(2), pp. 181-186, Feb. 1998.
Boldyreff, Gastric and intestinal mucus, its properties and physiological importance, Acta Medica Scandinavica (journal), vol. 89, Issue 1-2, pp. 1-14, Jan./Dec. 1936.
Borovikova et al., Acetylcholine inhibition of immune response to bacterial endotoxin in human macrophages, Abstracts, Society for Neuroscience, 29th Annual Meeting, Miami Beach, FL, Oct. 23-28, 1999, Abstract No. 624.6.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose than systemic treatment, 21st Annual Conference on Shock, San Antonio, TX, Jun. 14-17, 1998, Abstract No. 86.
Borovikova et al., Role of the efferent vagus nerve signaling in the regulation of the innate immune response to LPS, (supplemental to SHOCK, vol. 13, 2000, Molecular, cellular, and systemic pathobiological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioleigal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver Disease, vol. 19, No. 2, pp. 189-204, (year of pub. Sufficiently earlier than effective US filed and any foreign priority date) 1999.
Burke et al., Bent pseudoknots and novel RNA inhibitors of type 1 human immunodeficiency virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.

Cicala et al., "Linkage between inflammation and coagulation: An update on the molecular basis of the crosstalk," Life Sciences, vol. 62(20); pp. 1817-1824, Apr. 1998.
Cohen, "The immunopathogenesis of sepsis," Nature., vol. 420(6917): pp. 885-891, Dec. 2002.
Das, Critical advances in spticemia and septic shock, Critical Care, vol. 4, pp. 290-296, Sep. 7, 2000.
Del Signore et al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Doshi et al., Evolving role of tissue factor and its pathway inhibitor, Crit. Care Med., vol. 30, suppl. 5, pp. S241-S250, May 2002.
Ellington et al., In vitro selection of RNA molecules that bind specific ligands, Nature, vol. 346, pp. 818-822, Aug. 30, 1990.
Esmon, The protein C pathway, Crit. Care Med., vol. 28, suppl. 9, pp. S44-S48, Sep. 2000.
Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(-)-ET 126: A potent and selective M1 antagonist in vitro and in vivo, Life Sciences, vol. 58, No. 12, pp. 991-1000, Feb. 1996.
Goyal et al., Nature of the vagal inhibitory innervation to the lower esophageal sphincter, Journal of Clinical Investigation, vol. 55, pp. 1119-1126, May 1975.
Gracie, J. A., et al., A proinflammatory role for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Guslandi, M., Nicotine treatment for ulcerative colitis, Br. J. Clin. Pharmacol., vol. 48(4), pp. 481-484, Oct. 1999.
Harrison's Principles of Internal Medicine, 13th Ed., pp. 511-515 and 1433-1435, Mar. 1994.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; (year of pub. sufficiently earlier than effective US filed and any foreign priority date) 1980.
Holladay et al., Neuronal nicotinic acetylcholine receptors as targets for drug discovery, Journal of Medicinal Chemistry, 40(26), pp. 4169-4194, Dec. 1997.

(56) References Cited

OTHER PUBLICATIONS

Hommes, D. W. et al., Anti- and Pro-inflammatory cytokines in the pathogenesis of tissue damage in Crohn's disease, Current Opinion in Clinical Nutrition and Metabolic Care, vol. 3(3), pp. 191-195, May 2000.

Hsu, et al., Analysis of efficiency of magnetic stimulation, IEEE Trans. Biomed. Eng., vol. 50(11), pp. 1276-1285, Nov. 2003.

Hsu, H. Y., et al., Cytokine release of peripheral blood monoculear cells in children with chronic hepatitis B virus infection, J. Pediatr. Gastroenterol., vol. 29, No. 5, pp. 540-545, Nov. 1999.

Hu, et al., The effect of norepinephrine on endotoxin-mediated macrophage activation, J. Neuroimmunol., vol. 31(1), pp. 35-42, Jan. 1991.

Ilton et al., "Differential expression of neutrophil adhesion molecules during coronary artery surgery with cardiopulmonary bypass" Journal of Thoracic and Cardiovascular Surgery, Mosby-Year Book, inc., St. Louis, Mo, US, pp. 930-937, Nov. 1, 1999.

Jaeger et al., The structure of HIV-1 reverse transcriptase complexed with an RNA pseudoknot inhibitor, The EMBO Journal, 17(15), pp. 4535-4542, Aug. 1998.

Jander, S. et al., Interleukin-18 is induced in acute inflammatory demyelinating polymeuropathy, J. Neuroimmunol., vol. 114, pp. 253-258, Mar. 2001.

Joshi et al., Potent inhibition of human immunodeficiency virus type 1 replection by template analog reverse transcriptase, J. Virol., 76(13), pp. 6545-6557, Jul. 2002.

Kalishevskaya et al. "The character of vagotomy-and atropin-induced hypercoagulation," Sechenov Physiological Journal of the USSR, 65(3): pp. 398-404, Mar. 1979.

Kalishevskaya et al.; Nervous regulation of the fluid state of the blood; Usp. Fiziol. Nauk;,vol. 13; No. 2; pp. 93-122; Apr.-Jun. 1982.

Kanai, T. et al., Interleukin-18 and Crohn's disease, Digestion, vol. 63, suppl. 1, pp. 37-42, (year of pub. sufficiently earlier than effective US filed and any foreign priority date) 2001.

Katagiri, M., et al., Increased cytokine production by gastric mucosa in patients with helicobacter pylori infection, J. Clin, Gastroenterol., vol. 25, Suppl. 1, pp. S211-S214, (year of pub. sufficiently earlier than effective US filed and any foreign priority date) 1997.

Kawashima, et al., Extraneuronal cholinergic system in lymphocytes, Pharmacology & Therapeutics, vol. 86, pp. 29-48, Apr. 2000.

Kees et al; Via beta-adrenoceptors, stimulation of extrasplenic sympathetic nerve fibers inhibits lipopolysaccharide-induced TNF secretion in perfused rat spleen; J.Neuroimmunol.; 145(1-2); pp. 77-85; Dec. 2003.

Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.

Khatun, S., et al., "Induction of hypercoagulability condition by chronic localized cold stress in rabbits," Thromb. And Haemost., 81(3): pp. 449-455, Mar. 1999.

Kimball, et al., Levamisole causes differential cytokine expression by elicited mouse peritoneal macrophases, Journal of Leukocyte Biology, vo. 52, No. 3, pp. 349-356, Sep. 1992 (abstract only).

Kimmings, A. N., et al., Systemic inflammatory response in acute cholangitis and after subsequent treatment, Eur. J. Surg., vol. 166, pp. 700-705, Sep. 2000.

Kirchner et al.; Left vagus nerve stimulation suppresses experimentally induced pain; Neurology; vol. 55; pp. 1167-1171; Oct. 2000.

Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.

Krarup et al; Conduction studies in peripheral cat nerve using implanted electrodes: I. methods and findings in controls; Muscle & Nerve; vol. 11; pp. 922-932; Sep. 1988.

Kudrjashov, et al. "Reflex nature of the physiological anticoagulating system," Nature, vol. 196(4855): pp. 647-649; Nov. 17, 1962.

Kumins, N. H., et al., Partial hepatectomy reduces the endotoxin-induced peak circulating level of tumor necrosis factor in rats, SHOCK, vol. 5, No. 5, pp. 385-388, May 1996.

Kuznik, "Role of the vascular wall in the process of hemostatis," Usp Sovrem Biol., vol. 75(1): pp. 61-85, (year of pub. sufficiently earlier than effective US filed and any foreign priority date) 1973.

Kuznik, et al., "Blood Coagulation in stimulation of the vagus nerve in cats," Biull. Eskp. Biol. Med., vol. 78 (7): pp. 7-9, (year of pub. sufficiently earlier than effective US filed and any foreign priority date) 1974.

Kuznik, et al., "Heart as an efferent regulator of the process of blood coagulation and fibrinolysis," Kardiologiia, vol. 13(3): pp. 10-17, (year of pub. sufficiently earlier than effective US filed and any foreign priority date) 1973.

Kuznik, et al., "Role of the heart and vessels in regulating blood coagulation and fibrinolysis," Kagdiologiia, vol. 13 (4): pp. 145-154, (year of pub. sufficiently earlier than effective US filed and any foreign priority date) 1973.

Kuznik, et al., "Secretion of blood coagulation factors into saliva under conditions of hypo-and hypercoagulation," Voprosy Meditsinskoi Khimii, vol. 19(1): pp. 54-57; (year of pub. sufficiently earlier than effective US filed and any foreign priority date) 1973.

Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.

Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filed and any foreign priority date) 1975.

Lang, et al., "Neurogienic control of cerebral blood flow," Experimental Neurology, 43(1): pp. 143-161, Apr. 1974.

Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.

LeNovere, N. et al., Molecular evolution of the nicotinic acetylcholine receptor: an example of multigene family in excitable cells, J. Mol. Evol., 40, pp. 155-172, Feb. 1995.

Leonard, S. et al., Neuronal nicotinic receptors: from structure to function, Nicotine & Tobacco Res. 3:203-223, Aug. 2001.

Lipton, J. M. et al.; Anti-inflammatory actions of the neuroimmunomodulator ?-MSH, Immunol. Today, vol. 18, pp. 140-145, Mar. 1997.

Loeb et al.; Cuff electrodes for chronic stimulation and recording of peripheral nerve activity; Journal of Neuroscience Methods; vol. 64; pp. 95-103; Jan. 1996.

Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.

Martindale: The Extra Pharmacopoeia; 28th Ed. London; the pharmaceutical press; pp. 446-485; (year of pub. sufficiently earlier than effective US filed and any foreign priority date) 1982.

Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.

McGuinness, P. H., et al., Increases in intrahepatic CD68 positive cells, MAC387 positive cells, and proinflammatory cytokines (particulary interleukin 18) in chronic hepatitis C infection, Gut, vol. 46, pp. 260-269, (year of pub. sufficiently earlier than effective US filed and any foreign priority date) 2000.

Minnich et al.; Anti-cytokine and anti-inflammatory therapies for the treatment of severe sepsis: progress and pitfalls; Proceedings of the Nutrition Society; vol. 63(3); pp. 437-441; (year of pub. sufficiently earlier than effective US filed and any foreign priority date) 2004.

Mishchenko, et al., "Coagulation of the blood and fibrinolysos in dogs during vagal stimulation," Sechenov Physiological Journal of the USSR, vol. 61(1): pp. 101-107, (year of pub. sufficiently earlier than effective US filing date and any foreign priority date) 1975.

(56) References Cited

OTHER PUBLICATIONS

Mishchenko, "The role of specific adreno-and choline-receptors of the vascular wall in the regulation of blood coagulation in the stimulation of the vagus nerve," Biull. Eskp. Biol. Med., vol. 78(8): pp. 19-22, (year of pub. sufficiently earlier than effective US filed and any foreign priority date) 1974.

Molina et al., CNI-1493 attenuates hemodynamic and pro-inflammatory responses to LPS, Shock, vol. 10, No. 5, pp. 329-334, Nov. 1998.

Nadol et al., "Surgery of the Ear and Temporal Bone," Lippinkott Williams & Wilkins, 2nd Ed., 2005, (Publication date: Sep. 21, 2004), p. 580.

Nagashima et al., Thrombin-activatable fibrinolysis inhibitor (TAFI) deficiency is compatible with murine life, J. Clin. Invest., 109, pp. 101-110, Jan. 2002.

Nathan, C. F., Secretory products of macrophages, J. Clin. Invest., vol. 79 (2), pp. 319-326, Feb. 1987.

Navalkar et al.; Irbesartan, an angiotensin type 1 receptor inhibitor, regulates markers of inflammation in patients with premature atherosclerosis; Journal of the American College of Cardiology; vol. 37; No. 2; pp. 440-444; Feb. 2001.

Noguchi et al., Increases in Gastric acidity in response to electroacupuncture stimulation of hindlimb of anesthetized rats, Jpn. J. Physiol., 46(1), pp. 53-58, Feb. 1996.

Norton, Can ultrasound be used to stimulate nerve tissue, BioMedical Engineering OnLine, 2(1), pp. 6, Mar. 4, 2003.

Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.

Pateyuk, et al.,"Treatment of Botkin's disease with heparin," Klin. Med., vol. 51(3): pp. 113-117, Mar. 1973.

Payne, J. B. et al., Nicotine effects on PGE2 and IL-1 beta release by LPS-treated human monocytes, J. Perio. Res., vol. 31, No. 2, pp. 99-104, Feb. 1996.

Prystowsky, J. B. et al., Interleukin-1 mediates guinea pig gallbladder inflammation in vivo, J. Surg. Res., vol. 71, No. 2, pp. 123-126, Aug. 1997.

Pulkki, K. J., Cytokines and cardiomyocyte death, Ann. Med., vol. 29(4), pp. 339-343, Aug. 1997.

Pullan, R. D., et al., Transdermal nicotine for active ulceratiive colitis, N. Engl. J. Med., vol. 330, No. 12, pp. 811-5, Mar. 24, 1994.

Pulvirenti et al; Drug dependence as a disorder of neural plasticity:focus on dopamine and glutamate; Rev Neurosci.; vol. 12; No. 2; pp. 141-158; Apr./Jun. 2001.

Rayner, S. A. et al., Local bioactive tumour necrosis factor (TNF) in corneal allotransplantation, Clin. Exp. Immunol., vol. 122, pp. 109-116, Oct. 2000.

Rinner et al.; Rat lymphocytes produce and secrete acetylcholine in dependence of differentiation and activation; J.Neuroimmunol.; 81(1-2); pp. 31-37; Jan. 1998.

Robinson et al.; Studies with the Electrocardiograph on the Action of the Vagus Nerve on the Human Heart; J Exp Med; 14(3):217-234; Sep. 1911.

Romanovsky, A. A., et al.,The vagus nerve in the thermoregulatory response to systemic inflammation, Am. J. Physiol., vol. 273, No. 1 (part 2), pp. R407-R413, Jul. 1, 1997.

Saghizadeh et al.; The expression of TNF? by human muscle; J. Clin. Invest.; vol. 97; No. 4; pp. 1111-1116; Feb. 15, 1996.

Saindon et al.; Effect of cervical vagotomy on sympathetic nerve responses to peripheral interleukin-1beta; Auton.Neuroscience Basic and Clinical; 87; pp. 243-248; Mar. 23, 2001.

Saito, Involvement of muscarinic M1 receptor in the central pathway of the serotonin-induced bezold-jarisch reflex in rats, J. Autonomic Nervous System, vol. 49, pp. 61-68, Sep. 1994.

Sandborn, W. J., et al., Transdermal nicotine for mildly to moderately active ulcerative colitis, Ann. Intern. Med, vol. 126, No. 5, pp. 364-371, Mar. 1, 1997.

Sato, E., et al., Acetylcholine stimulates alveolar macrophages to release inflammatory cell chemotactic activity, Am. J. Physiol., vol. 274, pp. L970-L979, Jun. 1998.

Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1999.

Scheinman, R. I., et al., Role of transcriptional activation of 1?B? in mediation of immunosuppression by glucocorticoids, Science, vol. 270, No. 5234, pp. 283-286, Oct. 13, 1995.

Schneider et al., High-affinity ssDNA inhibitors of the review transcriptase of type 1 human immunodeficiency virus, Biochemistry, 34(29), pp. 9599-9610, (year of pub. sufficiently earlier than effective US filed and any foreign priority date) 1995.

Shafer, Genotypic testing for human immunodeficiency virus type 1 drug resistance, Clinical Microbiology Reviews, vol. 15, pp. 247-277, Apr. 2002.

Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.

Sher, M. E., et al., The influence of cigarette smoking on cytokine levels in patients with inflammatory bowel disease, Inflamm. Bowel Dis., vol. 5, No. 2, pp. 73-78, May 1999.

Shi et al.; Effects of efferent vagus nerve excitation on inflammatory response in heart tissue in rats with endotoxemia; vol. 15, No. 1; pp. 26-28; Jan. 2003 (Eng. Abstract).

Snyder et al., Correction of hemophilia B in canine and murine models using recombinant adeno-associated viral vectors; Nature Medicine, 5(1), pp. 64-70, Jan. 1999.

Sokratov, et al. "The role of choline and adrenegic structures in regulation of renal excretion of hemocoagulating compounds into the urine," Sechenov Physiological Journal of the USSR, vol. 63(12): pp. 1728-1732, (year of pub. sufficiently earlier than effective US filed and any foreign priority date) 1977.

Stalcup et al., Endothelial cell functions in the hemodynamic responses to stress, Annals of the New York Academy of Sciences, vol. 401, pp. 117-131, Dec. 1982.

Steinlein, New functions for nicotine acetylcholine receptors?, Behavioural Brain Res., vol. 95, pp. 31-35, (year of pub. sufficiently earlier than effective US filed and any foreign priority date) 1998.

Sternberg, E. M., Perspectives series: cytokines and the brain 'neural-immune interactions in health and disease,' J. Clin. Invest., vol. 100, No. 22, pp. 2641-2647, Dec. 1997.

Strojnik et al.; Treatment of drop foot using and implantable peroneal underknee stimulator; Scand. J. Rehab. Med.; vol. 19(1); pp. 37R43; (year of pub. sufficiently earlier than effective US filed and any foreign priority date) 1987.

Sugano et al., Nicotine inhibits the production of inflammatory mediators in U937 cells through modulation of nuclear factor-kappaβ activation, Biochemical and Biophysical Research Communications, vol. 252, No. 1, pp. 25-28, Nov. 9, 1998.

Sykes, et al., An investigation into the effect and mechanisms of action of nicotine in inflammatory bowel disease, Inflamm. Res., vol. 49, pp. 311-319, Jul. 2000.

Takeuchi et al., A comparision between chinese blended medicine "Shoseiryuto" tranilast and ketotifen on the anit-allergic action in the guinea pigs, Allergy, vol. 34, No. 6, pp. 387-393, Jun. 1985 (eng. abstract).

Toyabe, et al., Identification of nicotinic acetylcholine receptors on lymphocytes in the periphery as well as thymus in mice, Immunology, vol. 92(2), pp. 201-205, Oct. 1997.

Tracey et al., Mind over immunity, Faseb Journal, vol. 15, No. 9, pp. 1575-1576, Jul. 2001.

Tracey, K. J. et al., Anti-cachectin/TNF monoclonal antibodies prevent septic shock during lethal bacteraemia; Nature, 330: pp. 662-664, Dec. 23, 1987.

Tracey, K. J. et al., Shock and tissue injury induced by recombinant human cachectin, Science, vol. 234, pp. 470-474, Oct. 24, 1986.

Tracey, K.J., The inflammatory reflex, Nature, vol. 420, pp. 853-859, Dec. 19-26, 2002.

(56) References Cited

OTHER PUBLICATIONS

Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Vanhoutte, et al., Muscarinic and beta-adrenergic prejunctional modulation of adrenergic neurotransmission in the blood vessel wall, Gen Pharmac., vol. 14, pp. 35-37, (year of pub. sufficiently earlier than effective US filed and any foreign priority date) 1983.
Ventureyra, Transcutaneous vagus nerve stimulation for partial onset seizure therapy, Child's Nery Syst, vol. 16(2), pp. 101-102, (year of pub. sufficiently earlier than effective US filed and any foreign priority date) 2000.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von KäNel, et al., Effects of non-specific ?-adrenergic stimulation and blockade on blood coagulation in hypertension, J. Appl. Physiol., vol. 94, pp. 1455-1459, Apr. 2003.
Von KäNel, et al., Effects of sympathetic activation by adrenergic infusions on hemostasis in vivo, Eur. J. Haematol., vol. 65: pp. 357-369, Dec. 2000.
Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Weiner, et al., "Inflammation and therapeutic vaccination in CNS diseases," Nature., vol. 420(6917): pp. 879-884, Dec. 19-26, 2002.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yeh, S.S. et al., Geriatric cachexia: the role of cytokines, Am. J. Clin. Nutr., vol. 70(2), pp. 183-197, Aug. 1999.
Zhang et al., Tumor necrosis factor, The Cytokine Handbook, 3rd ed., Ed. Thompson, Academic Press, pp. 517-548, Jul. 1, 1998.
Clark et al.; Enhanced recognition memory following vagus nerve stimulation in human subjects; Nat. Neurosci.; 2(1); pp. 94-98; Jan. 1999.
Swick et al.; Locus coeruleus neuronal activity in awake monkeys: relationship to auditory P300-like potentials and spontaneous EEG. Exp. Brain Res.; 101(1); pp. 86-92; Sep. 1994.
Faltys et al.; U.S. Appl. No. 15/153,639 entitled "External programmer," filed May 12, 2016.
Cavaillon et al.; The pro-inflammatory cytokine casade; Immune Response in the Critically Ill; Springer-Verlag Berlin Hiedelberg; pp. 37-66; Jan. 21, 2002.
Faltys et al.; U.S. Appl. No. 15/406,619 entitled "Systems and methods for establishing a nerve block," filed Jan. 13, 2017.
Levine et al.; U.S. Appl. No. 15/411,933 entitled "Control of vagal stimulation," filed Jan. 20, 2017.
Zitnik et al.; U.S. Appl. No. 15/411,936 entitled "Implantable microstimulators and inductive charging systems," filed Jan. 20, 2017.
Faltys et al.; U.S. Appl. No. 15/415,764 entitled "Implantable neurostimulator having power control and thermal regulation and methods of use," filed Jan. 25, 2017.
Levine et al.; U.S. App. No. 15/853,350 entitled "Extremely low duty-cycle activation of the cholinergic anti-inflammatory pathway to treat chronic inflammation," filed Dec. 22, 2017.
Manta et al.; Optimization of vagus nerve stimulation parameters using the firing activity of serotonin neurons in the rat dorsal raphe; European Neuropsychopharmacology; vol. 19; pp. 250-255; Jan. 2009 (doi: 10.1016/j.euroneuro.2008.12.001).
Pongratz et al.; The sympathetic nervous response in inflammation; Arthritis Research and Therapy; 16(504); 12 pages; retrieved from the internet (http://arthritis-research.com/content/16/6/504) ; Jan. 2014.

\* cited by examiner

INHIBITION OF INFLAMMATORY CYTOKINE PRODUCTION BY CHOLINERGIC AGONISTS AND VAGUS NERVE STIMULATION

CROSS REFERENCE TO RELATED APPLICATIONS

This application is a continuation of U.S. patent application Ser. No. 10/990,938 filed on Nov. 17, 2004, titled "INHIBITION OF INFLAMMATORY CYTOKINE PRODUCTION BY CHOLINERGIC AGONISTS AND VAGUS NERVE STIMULATION," now U.S. Pat. No. 8,914,114, which is a continuation in part of U.S. patent application Ser. No. 10/446,625, filed on May 28, 2003, titled "INHIBITION OF INFLAMMATORY CYTOKINE PRODUCTION BY CHOLINERGIC AGONISTS AND VAGUS NERVE STIMULATION," now U.S. Pat. No. 6,838,471, which is a continuation of U.S. patent application Ser. No. 09/855,446, filed on May 15, 2001, titled "INHIBITION OF INFLAMMATORY CYTOKINE PRODUCTION BY CHOLINERGIC AGONISTS AND VAGUS NERVE STIMULATION," now U.S. Pat. No. 6,610,713, which claims priority to U.S. Provisional Patent Application No. 60/206,364, filed on May 23, 2000 and titled "VAGUS NERVE STIMULATION ATTENUATION OF THE SYSTEMIC INFLAMMATORY RESPONSE TO ENDOTOXIN." The entire teachings of the above applications are incorporated herein by reference.

BACKGROUND

1. Field of the Invention

The present invention generally relates to methods of reducing inflammation. More specifically, the invention relates to methods for reducing inflammation caused by proinflammatory cytokines or an inflammatory cytokine cascade.

2. Description of the Related Art

Vertebrates achieve internal homeostasis during infection or injury by balancing the activities of proinflammatory and anti-inflammatory pathways. However, in many disease conditions, this internal homeostasis becomes out of balance. For example, endotoxin (lipopolysaccharide, LPS) produced by all Gram-negative bacteria activates macrophages to release cytokines that are potentially lethal (44; 10; 47; 31).

Inflammation and other deleterious conditions (such as septic shock caused by endotoxin exposure) are often induced by proinflammatory cytokines, such as tumor necrosis factor (TNF; also known as TNF.alpha. or cachectin), interleukin (IL)-1.alpha., IL-1.beta., IL-6, IL-8, L-18, interferony, platelet-activating factor (PAF), macrophage migration inhibitory factor (MIF), and other compounds (42). Certain other compounds, for example high mobility group protein 1 (HMG-1), are induced during various conditions such as sepsis and can also serve as proinflammatory cytokines (57). These proinflammatory cytokines are produced by several different cell types, most importantly immune cells (for example monocytes, macrophages and neutrophils), but also non-immune cells such as fibroblasts, osteoblasts, smooth muscle cells, epithelial cells, and neurons (56). Proinflammatory cytokines contribute to various disorders, notably sepsis, through their release during an inflammatory cytokine cascade.

Inflammatory cytokine cascades contribute to deleterious characteristics, including inflammation and apoptosis (32), of numerous disorders. Included are disorders characterized by both localized and systemic reactions, including, without limitation, diseases involving the gastrointestinal tract and associated tissues (such as appendicitis, peptic, gastric and duodenal ulcers, peritonitis, pancreatitis, ulcerative, pseudomembranous, acute and ischemic colitis, diverticulitis, epiglottitis, achalasia, cholangitis, coeliac disease, cholecystitis, hepatitis, Crohn's disease, enteritis, and Whipple's disease); systemic or local inflammatory diseases and conditions (such as asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis); diseases involving the urogential system and associated tissues (such as septic abortion, epididymitis, vaginitis, prostatitis and urethritis); diseases involving the respiratory system and associated tissues (such as bronchitis, emphysema, rhinitis, cystic fibrosis, adult respiratory distress syndrome, pneumonitis, pneumoultramicroscopicsilicov-olcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as burns, dermatitis, dermatomyositis, sunburn, urticaria warts. and wheals); diseases involving the cardiovascular system and associated tissues (such as vasulitis, angiitis, endocarditis, arteritis, atherosclerosis, thrombophlebitis, pericarditis, myocarditis, myocardial ischemia, congestive heart failure, periarteritis nodosa, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Berger's disease, and Retier's syndrome); as well as various cancers, tumors and proliferative disorders (such as Hodgkins disease); and, in any case the inflammatory or immune host response to any primary disease (13; 55; 30; 20; 33; 25; 18; 27; 48; 24; 7; 9; 4; 3; 12; 8; 19; 15; 23; 49; 34).

Mammals respond to inflammation caused by inflammatory cytokine cascades in part through central nervous system regulation. This response has been characterized in detail with respect to systemic humoral response mechanisms during inflammatory responses to endotoxin (2; 54; 21; 28). In one set of responses, afferent vagus nerve fibers are activated by endotoxin or cytokines, stimulating the release of humoral anti-inflammatory responses through glucocorticoid hormone release (51; 41; 39). Previous work elucidated a role for vagus nerve signaling as a critical component in the afferent loop that modulates the adrenocorticotropin and fever responses to systemic endotoxemia and cytokinemia (14; 11; 52; 35). However, comparatively little is known about the role of efferent neural pathways that can modulate inflammation.

Efferent vagus nerve signaling has been implicated in facilitating lymphocyte release from thymus via a nicotinic acetylcholine receptor response (1). Clinical studies have also indicated that nicotine administration can be effective for treating some cases of inflammatory bowel disease (17; 36), and that proinflammatory cytokine levels are significantly decreased in the colonic mucosa of smokers with inflammatory bowel disease (40). However, none of these findings would suggest that cholinergic agonists can inhibit an inflammatory cytokine cascade, particularly those mediated by macrophages. Also, there is no suggestion in the literature that efferent vagus nerve stimulation is effective in inhibiting these cascades.

SUMMARY OF THE DISCLOSURE

Accordingly, the inventor has succeeded in discovering that cholinergic agonists can inhibit the release of proinflammatory cytokines from a mammalian cell, either in vitro or in vivo. This inhibitory effect is useful for inhibiting inflammatory cytokine cascades that mediate many disease conditions. Furthermore, cholinergic agonist treatment in vivo can be effected to inhibit either local or systemic inflammatory cytokine cascades by stimulating efferent vagus nerves.

Thus, one embodiment of the present invention is directed to a method of inhibiting the release of a proinflammatory cytokine from a mammalian cell. The method comprises treating the cell with a cholinergic agonist in an amount sufficient to decrease the amount of the proinflammatory cytokine that is released from the cell. In preferred embodiments, the cell is a macrophage. Preferably, the proinflammatory cytokine is tumor necrosis factor (TNF), interleukin (IL)-1.beta., IL-6, IL-18 or HMG-1, most preferably TNF. In preferred embodiments, the cholinergic agonist is acetylcholine, nicotine, muscarine, carbachol, galantamine, arecoline, cevimeline, or levamisole. In other preferred embodiments, the cell is in a patient suffering from, or at risk for, a condition mediated by an inflammatory cytokine cascade, preferably appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, coeliac disease, congestive heart failure, adult respiratory distress syndrome, Alzheimer's disease, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Berger's disease, Retier's syndrome, or Hodgkins disease. In more preferred embodiments, the condition is appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. In the most preferred embodiments, the condition is endotoxic shock. In some embodiments, the cholinergic agonist treatment is effected by stimulating efferent vagus nerve activity sufficient to inhibit the inflammatory cytokine cascade. Preferably, the efferent vagus nerve activity is stimulated electrically. The efferent vagus nerve can be stimulated without stimulating the afferent vagus nerve. Vagus nerve ganglions or postganglionic neurons can also be stimulated. Additionally, peripheral tissues or organs that are served by the vagus nerve can also be stimulated directly.

The present invention is also directed to a method of inhibiting an inflammatory cytokine cascade in a patient. The method comprises treating the patient with a cholinergic agonist in an amount sufficient to inhibit the inflammatory cytokine cascade, wherein the patient is suffering from, or at risk for, a condition mediated by the inflammatory cytokine cascade. The cholinergic agonist is preferably acetylcholine, nicotine, muscarine, carbachol, galantamine, arecoline, cevimeline, or levamisole, and the condition is preferably appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis-alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graftversus-host disease, Type I diabetes, ankylosing spondylitis, Berger's disease, Type I diabetes, ankylosing spondylitis, Berger's disease, Retier's syndrome, or Hodgkins disease. In more preferred embodiments, the condition is appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. In the most preferred embodiments, the condition is endotoxic shock. The cholinergic agonist treatment can be effected by stimulating efferent vagus nerve activity, preferably electrically.

In additional embodiments, the present invention is directed to a method for treating a patient suffering from, or at risk for, a condition mediated by an inflammatory cytokine cascade. The method comprises stimulating efferent vagus nerve activity of the patient sufficient to inhibit the inflammatory cytokine cascade. Preferred methods of stimulation and preferred conditions are as with the previously described methods.

In still other embodiments, the present invention is directed to a method for attenuation of a systemic inflammatory response to endotoxin in a patient. The method comprises stimulating efferent vagus nerve activity of the patient sufficient to inhibit an inflammatory cytokine cascade.

The present invention is additionally directed to a method for determining whether a compound is a cholinergic agonist. The method comprises determining whether the compound inhibits the release of a proinflammatory cytokine from a mammalian cell. In preferred embodiments the cell is a macrophage and the proinflammatory cytokine is TNF.

DETAILED DESCRIPTION

Figure 1:
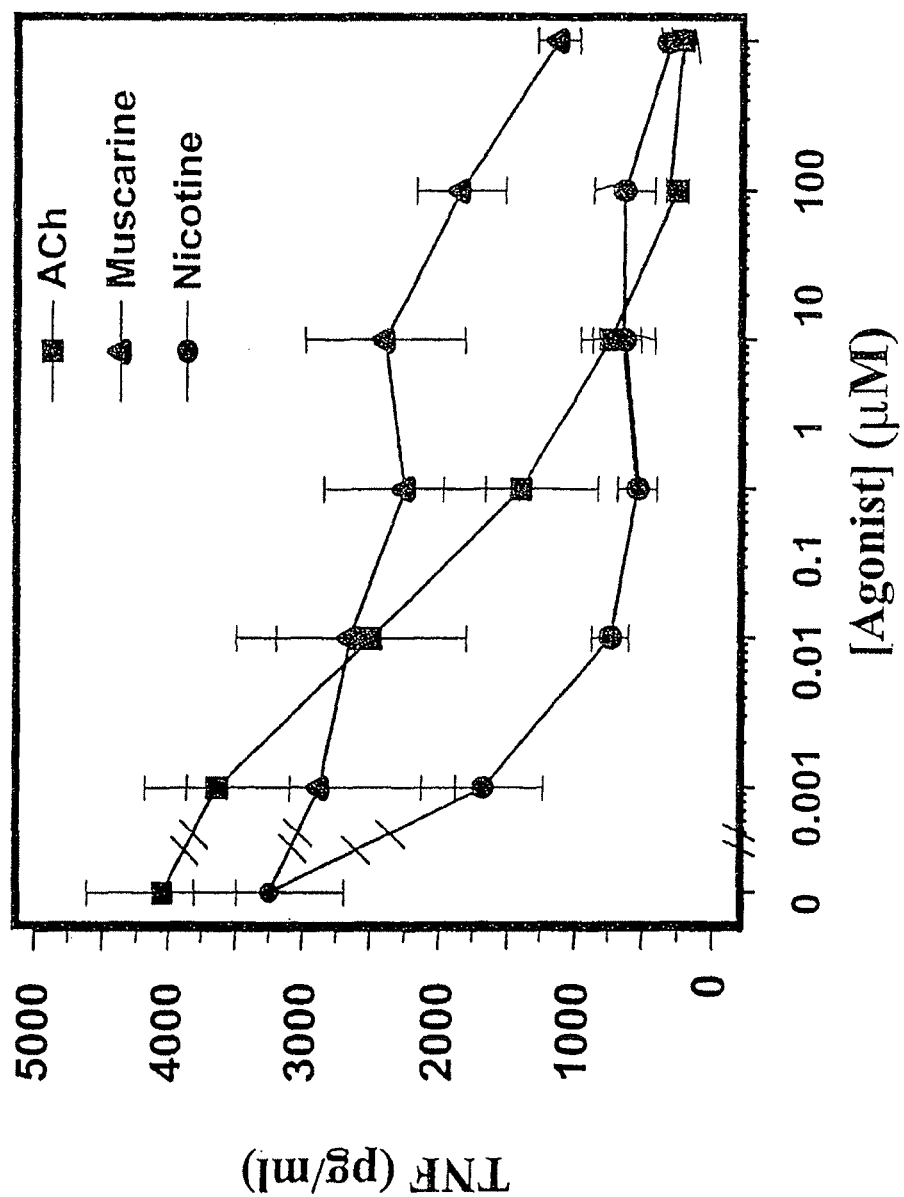
FIG. 1 is a graph summarizing experimental results showing that cholinergic agonists inhibit release of TNF from human macrophage cultures in a dose-dependent manner. Acetylcholine (ACh), muscarine, or nicotine was added to human macrophage cultures at the concentrations indicated, followed by LPS addition for 4 hours. TNF concentration was then determined.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes).

The present invention is based on the discovery that treatment of a proinflammatory cytokine-producing cell with a cholinergic agonist attenuates the release of proinflammatory cytokines from that cell, and that this attenuation process can be utilized in treatments for disorders mediated by an inflammatory cytokine cascade (5-6). It has further been discovered that stimulation of efferent vagus nerve fibers releases sufficient acetylcholine to stop a systemic inflammatory cytokine cascade, as occurs in endotoxic shock (5), or a localized inflammatory cytokine cascade (6). The efferent vagus nerve stimulation can also inhibit a localized inflammatory cytokine cascade in tissues and organs that are served by efferent vagus nerve fibers.

Accordingly, in some embodiments the present invention is directed to methods of inhibiting the release of a proinflammatory cytokine from a mammalian cell. The methods comprise treating the cell with a cholinergic agonist in an amount sufficient to decrease the amount of the proinflammatory cytokine released from the cell.

As used herein, a cytokine is a soluble protein or peptide which is naturally produced by mammalian cells and which act in vivo as humoral regulators at micro- to picomolar concentrations. Cytokines can, either under normal or pathological conditions, modulate the functional activities of individual cells and tissues. A proinflammatory cytokine is a cytokine that is capable of causing any of the following physiological reactions associated with inflammation: vasodialation, hyperemia, increased permeability of vessels with associated edema, accumulation of granulocytes and mononuclear phagocytes, or deposition of fibrin. In some cases, the proinflammatory cytokine can also cause apoptosis, such as in chronic heart failure, where TNF has been shown to stimulate cardiomyocyte apoptosis (32; 45). Nonlimiting examples of proinflammatory cytokines are tumor necrosis factor (TNF), interleukin (IL)-1.alpha., IL-1.beta., IL-6, IL-8, IL-18, interferon.gamma., HMG-1, platelet-activating factor (PAF), and macrophage migration inhibitory factor (MIF). In preferred embodiments of the invention, the proinflammatory cytokine that is inhibited by cholinergic agonist treatment is TNF, an IL-1, IL-6 or IL-18, because these cytokines are produced by macrophages and mediate deleterious conditions for many important disorders, for example endotoxic shock, asthma, rheumatoid arthritis, inflammatory bile disease, heart failure, and allograft rejection. In most preferred embodiments, the proinflammatory cytokine is TNF.

Proinflammatory cytokines are to be distinguished from anti-inflammatory cytokines, such as IL-4, IL-10, and IL-13, which are not mediators of inflammation. In preferred embodiments, release of anti-inflammatory cytokines is not inhibited by cholinergic agonists.

In many instances, proinflammatory cytokines are produced in an inflammatory cytokine cascade, defined herein as an in vivo release of at least one proinflammatory cytokine in a mammal, wherein the cytokine release affects a physiological condition of the mammal. Thus, an inflammatory cytokine cascade is inhibited in embodiments of the invention where proinflammatory cytokine release causes a deleterious physiological condition.

Any mammalian cell that produces proinflammatory cytokines are useful for the practice of the invention. Nonlimiting examples are monocytes, macrophages, neutrophils, epithelial cells, osteoblasts, fibroblasts, smooth muscle cells, and neurons. In preferred embodiments, the cell is a macrophage.

As used herein, a cholinergic agonist is a compound that binds to cells expressing cholinergic receptor activity. The skilled artisan can determine whether any particular compound is a cholinergic agonist by any of several well-known methods.

When referring to the effect of the cholinergic agonist on release of proinflammatory cytokines or an inflammatory cytokine cascade, or the effect of vagus nerve stimulation on an inflammatory cytokine cascade, the use of the terms "inhibit" or "decrease" encompasses at least a small but measurable reduction in proinflammatory cytokine release. In preferred embodiments, the release of the proinflammatory cytokine is inhibited by at least 20% over non-treated controls; in more preferred embodiments, the inhibition is at least 50%; in still more preferred embodiments, the inhibition is at least 70%, and in the most preferred embodiments, the inhibition is at least 80%. Such reductions in proinflammatory cytokine release are capable of reducing the deleterious effects of an inflammatory cytokine cascade in in vivo embodiments.

Any cholinergic agonist, now known or later discovered, would be expected to inhibit the release of proinflammatory cytokines from mammalian cells. In preferred embodiments, the cholinergic agonist is not otherwise toxic to the cell at useful concentrations. In more preferred embodiments, the cholinergic agonist has been used therapeutically in vivo or is naturally produced by mammalian cells. Nonlimiting examples include acetylcholine, nicotine, muscarine, carbachol, galantamine, arecoline, cevimeline, and levamisole. In most preferred in vitro embodiments, the cholinergic agonist is acetylcholine, nicotine, or muscarine. In in vivo embodiments, acetylcholine is not preferred because the compound would be expected to be inactivated very quickly due to the widespread occurrence of acetylcholinesterase in tissues.

The present invention is useful for studying cells in culture, for example studying the effect of inflammatory cytokine release on the biology of macrophages, or for testing compounds for cholinergic agonist activity. However, in vivo applications make up many of the preferred embodiments. In those embodiments, the cell is in a patient suffering from, or at risk for, a condition mediated by an inflammatory cytokine cascade. As used herein, a patient can be any mammal. However, in preferred embodiments, the patient is a human.

The treatment of any condition mediated by an inflammatory cytokine cascade is within the scope of the invention. In preferred embodiments, the condition is one where the inflammatory cytokine cascade is affected through release of proinflammatory cytokines from a macrophage. The condition can be one where the inflammatory cytokine cascade causes a systemic reaction, such as with septic shock. Alternatively, the condition can be mediated by a localized inflammatory cytokine cascade, as in rheumatoid arthritis. Nonlimiting examples of conditions which can be usefully treated using the present invention include those conditions enumerated in the background section of this specification. Preferably, the condition is appendicitis, peptic, gastric or duodenal ulcers, peritonitis, pancreatitis, ulcerative, pseudomembranous, acute or ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis-, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, coeliac disease, congestive heart failure, adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Type I diabetes, ankylosing spondylitis, Berger's disease, Retier's syndrome, or Hodgkins disease. In more preferred embodiments, the condition is appendicitis, peptic, gastric or duodenal ulcers, peritonitis, pancreatitis, ulcerative, pseudomembranous, acute or ischemic colitis, hepatitis, Crohn's disease, asthma, allergy, anaphylactic shock, organ ischemia, reperfusion injury, organ necrosis, hay fever, sepsis, septicemia, endotoxic shock, cachexia, septic abortion, disseminated bacteremia, burns, Alzheimer's disease, coeliac disease, congestive heart failure, adult respiratory distress syndrome, cerebral infarction, cerebral embolism, spinal cord injury, paralysis, allograft rejection or graft-versus-host disease. In the most preferred embodiments, the condition is endotoxic shock.

The route of administration of the cholinergic agonist depends on the condition to be treated. For example, intravenous injection may be preferred for treatment of a systemic disorder such as septic shock, and oral administration may be preferred to treat a gastrointestinal disorder such as a gastric ulcer. The route of administration and the dosage of the cholinergic agonist to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the cholinergic agonist can be administered orally, parenterally, intranasally, vaginally, rectally, lingually, sublingually, bucally, intrabuccaly and transdermally to the patient.

Accordingly, cholinergic agonist compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

Cholinergic agonist compositions of the present invention can easily be administered parenterally such as for example, by intravenous, intramuscular, intrathecal or subcutaneous injection. Parenteral administration can be accomplished by incorporating the cholinergic agonist compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120.degree. C., dissolving the cholinergic agonist in the glycerin, mixing the heated glycerin after which purified water may be added, and pouring the hot mixture into a suppository mold.

Transdermal administration includes percutaneous absorption of the cholinergic agonist through the skin. Transdermal formulations include patches (such as the well-known nicotine patch), ointments, creams, gels, salves and the like.

The present invention includes nasally administering to the mammal a therapeutically effective amount of the cholinergic agonist. As used herein, nasally administering or nasal administration includes administering the cholinergic agonist to the mucous membranes of the nasal passage or nasal cavity of the patient. As used herein, pharmaceutical compositions for nasal administration of a cholinergic agonist include therapeutically effective amounts of the agonist prepared by well-known methods to be administered, for example, as a nasal spray, nasal drop, suspension, gel, ointment, cream or powder. Administration of the cholinergic agonist may also take place using a nasal tampon or nasal sponge.

In accordance with the present invention, it has also been discovered that the cholinergic agonist can be administered to the patient in the form of acetylcholine by stimulating efferent vagus nerve fibers. As is well known, efferent vagus nerve fibers secrete acetylcholine upon stimulation. Such stimulation releases sufficient acetylcholine to be effective in inhibiting a systemic inflammatory cytokine cascade as well as a localized inflammatory cytokine cascade in a tissue or organ that is served by efferent branches of the vagus nerve, including the pharynx, the larynx, the esophagus, the heart, the lungs, the stomach, the pancreas, the spleen, the kidneys, the adrenal glands, the small and large intestine, the colon, and the liver.

The effect of vagus nerve stimulation on the inhibition of inflammatory cytokine cascades is not necessarily limited to that caused by acetylcholine release. The scope of the invention also encompasses any other mechanism that is partly or wholly responsible for the inhibition of inflammatory cytokine cascades by vagus nerve stimulation. Nonlimiting examples include the release of serotonin agonists or stimulation of other neurotransmitters.

As used herein, the vagus nerve is used in its broadest sense, and includes any nerves that branch off from the main vagus nerve, as well as ganglions or postganglionic neurons that are connected to the vagus nerve. The vagus nerve is also known in the art as the parasympathetic nervous system and its branches, and the cholinergic nerve.

The efferent vagus nerve fibers can be stimulated by any means. Nonlimiting examples include: mechanical means such as a needle, ultrasound, or vibration. Mechanical stimulation can also be carried out by carotid massage, oculocardiac reflex, dive reflex and valsalva maneuver. Specific examples where an inflammatory response was reduced by mechanical vagal nerve stimulation are provided in Examples 5 and 6. The efferent vagal nerve fibers can also be stimulated by electromagnetic radiation such as infrared, visible or ultraviolet light; heat, or any other energy source. In preferred embodiments, the vagus nerve is stimulated electrically, using for example a commercial vagus nerve stimulator such as the Cyberonics NCP®, or an electric probe. The efferent vagus nerve can be stimulated by stimulating the entire vagus nerve (i.e., both the afferent and efferent nerves), or by isolating efferent nerves and stimulating them directly. The latter method can be accomplished by separating the afferent from the efferent fibers in an area of the nerve where both types of fibers are present. Alternatively, the efferent fiber is stimulated where no afferent fibers are present, for example close to the target organ served by the efferent fibers. The efferent fibers can also be stimulated by stimulating the target organ directly, e.g., electrically, thus stimulating the efferent fibers that serve that organ. In other embodiments, the ganglion or postganglionic neurons of the vagus nerve can be stimulated. The vagus nerve can also be cut and the distal end can be stimulated, thus only stimulating efferent vagus nerve fibers (see, e.g., Example 2).

The amount of stimulation useful to inhibit an inflammatory cytokine cascade can be determined by the skilled artisan without undue experimentation for any condition to be treated. To inhibit a systemic inflammatory cytokine cascade, as induced with endotoxin, constant voltage stimuli of 1 to 5 V, at 2 ms and 1 Hz, for 10 min. before exposure and 10 min. after exposure, will inhibit the systemic inflammatory cytokine cascade sufficiently to prevent death of the subject by endotoxic shock (see Examples 2 and 3).

In other embodiments, the invention is directed to methods of inhibiting an inflammatory cytokine cascade in a patient. The methods comprise treating the patient with a cholinergic agonist in an amount sufficient to inhibit the inflammatory cytokine cascade. In preferred embodiments, the patient is suffering from, or at risk for, a condition mediated by the inflammatory cytokine cascade.

Cholinergic agonists useful for these embodiments have been previously discussed and include acetylcholine, nicotine, muscarine, carbachol, galantamine, arecoline, cevimeline, and levamisole. Also as previously discussed, acetylcholine can be administered by stimulating efferent vagus nerve fibers.

In additional embodiments, the present invention is directed to a method for treating a patient suffering from, or at risk for, a condition mediated by an inflammatory cytokine cascade. The method comprises stimulating efferent vagus nerve activity sufficient to inhibit the inflammatory cytokine cascade. Methods for stimulating efferent vagus nerve fibers have been previously discussed.

The present invention is also directed to methods for determining whether a compound is a cholinergic agonist. The method comprises determining whether the compound inhibits the release of a proinflammatory cytokine from a mammalian cell.

For this method, the cell can be any cell that can be induced to produce a proinflammatory cytokine. In preferred embodiments, the cell is an immune cell, for example macrophages, monocytes, or neutrophils. In the most preferred embodiments, the cell is a macrophage.

The proinflammatory cytokine to be measured for inhibition can be any proinflammatory cytokine that can be induced to be released from the cell. In preferred embodiments, the cytokine is TNF. Evaluation of the inhibition of cytokine production can be by any means known, including quantitation of the cytokine (e.g., with ELISA), or by bioassay, (e.g. determining whether proinflammatory cytokine activity is reduced).

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

Cholinergic Agonists Inhibit Release of Proinflammatory Cytokines from Macrophages 1. Materials and Methods Human macrophage cultures were prepared as follows. Buffy coats were collected from the blood of healthy individual donors to the Long Island Blood Bank Services (Melville, N.Y.). Primary blood mononuclear cells were isolated by density-gradient centrifugation through Ficoll/Hypaque (Pharmacia, N.J.), suspended ($8.times.10.sup.6$ cells/ml) in RPMI 1640 medium supplemented with 10% heat inactivated human serum (Gemini Bio-Products, Inc., Calabasas, Calif.), and seeded in flasks (PRIMARIA; Beckton and Dickinson Labware, Franklin Lakes, N.J.). After incubation for 2 hours at 37.degree. C., adherent cells were washed extensively, treated briefly with 10 mM EDTA, detached, resuspended ($10.sup.6$ cells/ml) in RPMI medium (10% human serum), supplemented with human macrophage colony stimulating factor (MCSF; Sigma Chemical Co., St. Louis, Mo.; 2 ng/ml), and seeded onto 24-well tissue culture plates (PRIMARIA; Falcon) ($10.sup.6$ cells/well). Cells were allowed to differentiate for 7 days in the presence of MCSF. On day 7 the cells were washed 3 times with 1.times. Dulbecco's phosphate buffered saline (PBS, GibcoBRL, Life Technologies, Rockville, Md.), fresh medium devoid of MCSF was added, and experiments performed as indicated.

RNase protection assays were performed as follows. Total RNA was isolated from cultured cells by using TRIzol reagent (GIBCO BRL, Rockville, Md.) following the manufacturer's instructions, and electrophoresed on 1.2% agarose/17% formaldehyde gel for verification of the integrity of the RNA samples. The RNase protection assay was conducted using a kit obtained from PharMingen (San Diego, Calif.). The anti-sense RNA probe set (hck-3) was labeled with [$a\text{-}.sup.32P$] UTP (Sp.Act. 800 Ci/mmol, Amersham, Arlington Heights, Ill.) using T7 RNA polymerase. Molecular weight markers were prepared by using pBR-322 plasmid DNA digested with MSP I (New England Bio Labs, Beverly, Mass.) and end-labeled using [$a\text{-}.sup.32P$] dCTP (Sp. Act. 800 Ci/mmol, Amersham, Arlington Heights, Ill.) with Klenow enzyme (Strategene, La Jolla, Calif.).

TNF immunohistochemistry was performed as follows. Human macrophages were differentiated as described above, and grown on glass chamber slides (Nunc, Naperville, Ill.). Slides were incubated in a blocking solution (1% BSA, 5% normal goat serum, 0.3% Triton X-100 in PBS) for 1 hour at room temperature and then incubated for 24 hours at 4.degree. C. with a primary mouse anti-human TNF monoclonal antibody (Genzyme, Cambridge, Mass.) diluted 1:100 in PBS containing 0.3% Triton X-100, 0.1% BSA, and 3% normal goat serum. Washed sections were incubated for 2 hours with secondary biotinylated anti-mouse IgG (1:200, Vector Laboratories, Inc., Burlingame, Calif.). The reaction product was visualized with 0.003% hydrogen peroxide and 0.05% 3,3'-diaminobenzidine tetrahydrochloride as a chromogen. Negative controls were incubated in the absence of primary antibodies (not shown). Slides were analyzed on a light microscope (Olympus BX60, Japan) using a MetaMorth Imaging System (Universal Imaging Co., West Chester, Pa.).

2. Results

Primary human macrophage cultures were established by incubating human peripheral blood mononuclear cells in the presence of macrophage colony stimulating factor (MCSF; Sigma Chemical Co., St. Louis, Mo.). These cells were used in experiments to determine the effects of cholinergic agonists on TNF levels in macrophage cultures conditioned by exposure to LPS for 4 hours (FIG. 1). In those experiments, acetylcholine chloride (ACh; Sigma Chemical Co., St. Louis, Mo.) was added to human macrophage cultures at the indicated concentrations (squares) in the presence of the acetylcholinesterase inhibitor pyridostigmine bromide (1 mM, Sigma Chemical Co., St. Louis, Mo.). Muscarine (triangles) and nicotine (circles) (Sigma Chemical Co., St. Louis, Mo.) were added in the concentrations indicated (FIG. 1). LPS was added five minutes later (100 ng/ml), and conditioned supernatants collected after 4 hours of stimulation for subsequent analysis by TNF enzyme-linked immunosorbent assay (ELISA). All the experimental conditions were performed in triplicate. Data from nine separate macrophage preparations are shown as Mean.+−.SEM; n=9.

As shown in FIG. 1, acetylcholine, nicotine, and muscarine all inhibited TNF release in a dose dependent manner. Comparable inhibition of TNF release by acetylcholine was observed in macrophage culture media conditioned by exposure to LPS for 20 hours (not shown), indicating that the inhibitory effect of acetylcholine on TNF did not merely delay the onset of the TNF response. Inhibition of TNF was also observed in macrophage cultures treated with carbachol, a chemically distinct cholinergic agonist (not shown).

The molecular mechanism of TNF inhibition was investigated by measuring TNF mRNA levels in an RNase protection assay. In those experiments (FIG. 2), macrophages were incubated in the presence of ACh (100.mu.M), muscarine (Mus, 100.mu.M), nicotine (Nic, 100.mu.M) or medium alone for 5 minutes followed by 2 hour exposure to LPS (100 ng/ml). ACh was added with pyridostigmine bromide (1 mM). Control wells were incubated with medium alone for 2 hours. Expression of the GAPDH gene product was measured to control for mRNA loading.

Figure 2:
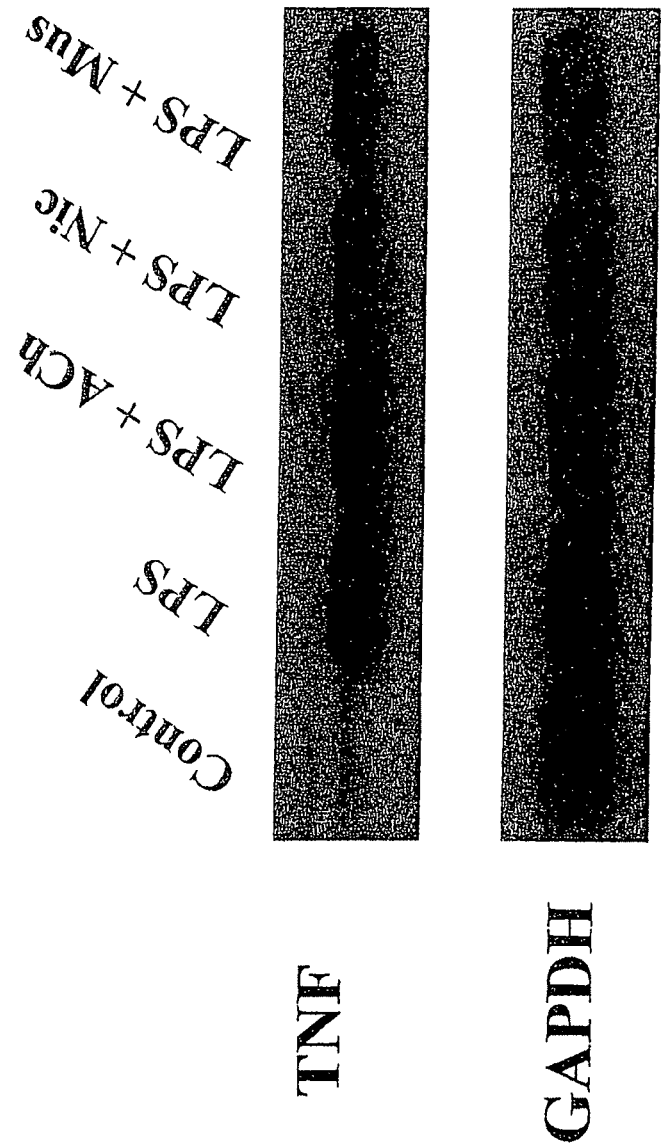
FIG. 2 shows autoradiographs of TNF or GADPH mRNA from LPS-stimulated human macrophages treated with acetylcholine (ACh), nicotine (Nic) or muscarine (Mus), or no cholinergic agonist, which demonstrate that cholinergic agonists do not reduce LPS-stimulated TNF mRNA levels in macrophages.

TNF mRNA levels in acetylcholine-treated, LPS-stimulated macrophages did not decrease as compared to vehicle-treated, LPS-stimulated macrophages, even when acetylcholine was added in concentrations that inhibited TNF protein release (FIG. 2). This indicates that acetylcholine suppresses TNF release through a post-transcriptional mechanism.

To determine whether acetylcholine inhibited macrophage TNF synthesis or macrophage TNF release, monoclonal anti-TNF antibodies were used to label cell-associated TNF in human macrophage cultures. In those experiments (FIG. 3), cells were exposed to either ACh (100.mu.M), either alone or in the presence of pyridostigmine bromide (1 mM), five minutes before LPS (100 ng/ml) treatment. Two hours later the cells were fixed in buffered 10% formalin and subjected to immunocytochemical analysis using primary mouse anti-hTNF monoclonal antibodies as described in Materials and Methods.

Figure 3:
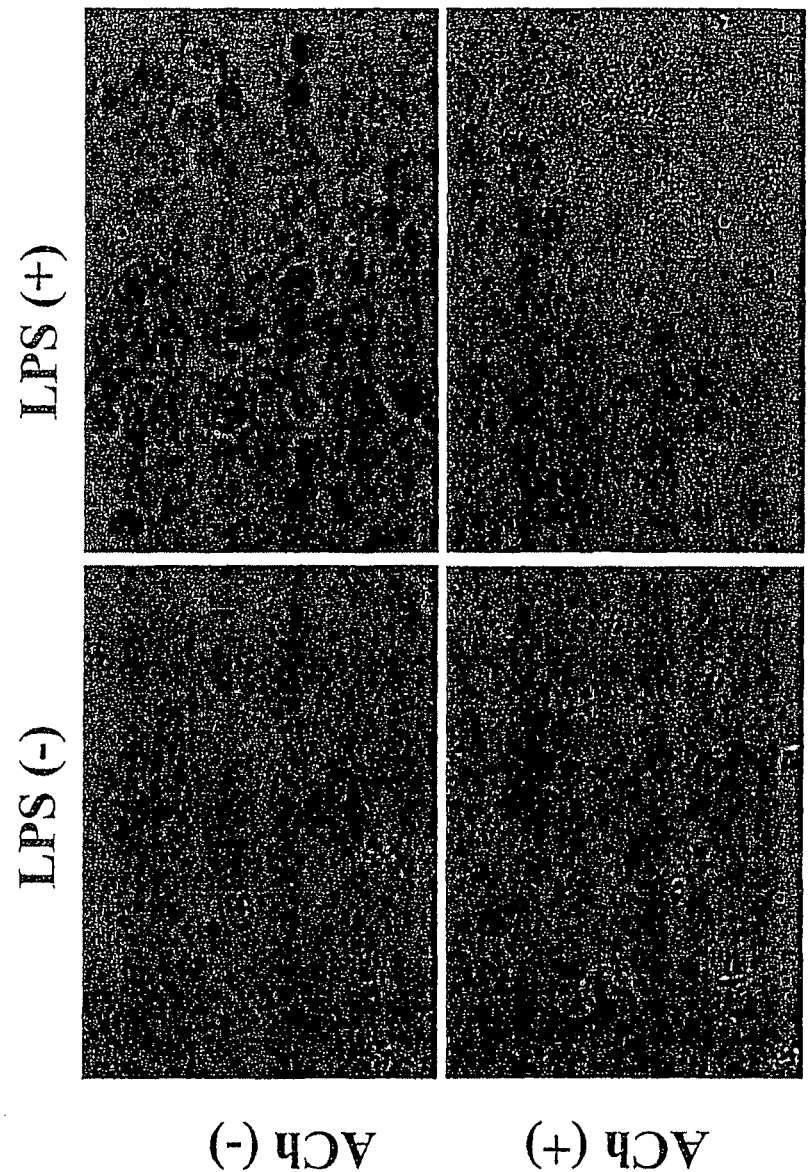
FIG. 3 shows micrographs of human macrophages stained with TNF antibodies demonstrating the effect of LPS and/or acetylcholine (ACh) treatment on TNF presence in the cells.

Those experiments established that acetylcholine significantly attenuated the appearance of LPS-stimulated TNF immunoreactivity in macrophages (FIG. 3). Considered together, these results indicate that the inhibitory effect of acetylcholine on human macrophage TNF production occurs through the post-transcriptional suppression of TNF protein synthesis, or possibly through an increased rate of degradation of intracellular TNF (FIG. 3).

Previous work indicated that peripheral blood mononuclear cells express nicotinic and muscarinic acetylcholine receptors (37-38; 53). To define pharmacologically the type of macrophage cholinergic receptor activities involved in modulating the TNF response, the results in FIG. 1 were further analyzed. Nicotine significantly inhibited TNF release in a dose-dependent manner; the effective concentration of nicotine that inhibited 50% of the TNF response ($E.C._{.50}$) was estimated to be 8.3.+−.7.1 nM (n=9). This $E.C._{.50}$ for nicotine compared favorably with the $E.C._{.50}$ for acetylcholine-mediated inhibition of TNF (acetylcholine $E.C._{.50}$=20.2.+−.8.7 nM, n=9). Muscarine also significantly inhibited TNF release, although it was a much less effective inhibitor of macrophage TNF as compared to either acetylcholine or nicotine (muscarine $E.C._{.50}$=42.4.+−.18.6 mM, n=9; P<0.01 vs nicotine or acetylcholine).

Figure 4:
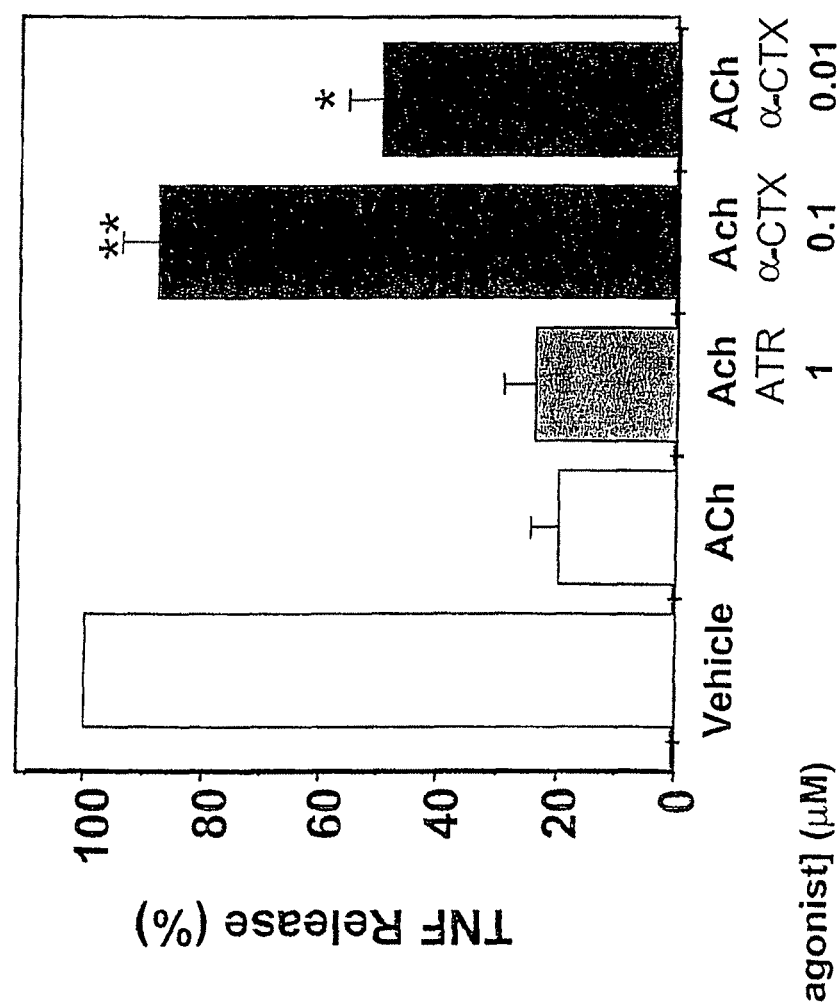
FIG. 4 is a graph summarizing experimental results showing that .alpha.-conotoxin (.alpha.-CTX), but not atropine (ATR), reverses the inhibitory effect of acetylcholine (ACh)-mediated inhibition of TNF in human macrophages.

To establish whether acetylcholine inhibited TNF primarily through the activity of nicotinic or muscarinic acetylcholine receptors, the specific muscarinic antagonist, atropine, was added to LPS-stimulated macrophage cultures that were co-treated with acetylcholine (FIG. 4). I also addressed whether the nicotinic acetylcholine receptor activity that mediated inhibition of TNF was a-bungarotoxin-sensitive or a-bungarotoxin-insensitive (FIG. 4). Conditions for macrophage culture and TNF assays were as previously described. Atropine (striped bars) (1 mM; Sigma Chemical Co., St. Louis, Mo.) or .alpha.-conotoxin (black bars) (0.1, 0.01 mM; Oncogene Research Products, Cambridge, Mass.) were added to macrophage cultures 5 minutes prior to acetylcholine (10.mu.M) and LPS (100 ng/ml). Data shown are Mean.+−.SEM of 3 separate experiments using different macrophages prepared from separate donors.

Addition of atropine, even in concentrations as high as 1 mM, failed to restore TNF release in acetylcholine-treated macrophage cultures (FIG. 4). Note that Acetylcholine inhibited TNF release by 80%, but this was not reversed by atropine. However, addition of .alpha.-conotoxin to acetylcholine-treated LPS-stimulated macrophage cultures significantly reversed the inhibitory effect of acetylcholine in a dose dependent manner (FIG. 4). (**P<0.005 vs ACh; *P<0.05 vs ACh). Neither atropine nor .alpha.-conotoxin altered TNF production in vehicle-treated cultures (not shown). Considered together, these data provide evidence that the inhibitory effect of acetylcholine on the LPS-induced TNF response in human macrophage cultures is mediated primarily by .alpha.-bungarotoxin-sensitive, nicotinic acetylcholine receptors. Acetylcholine levels in mammalian tissues can reach the millimolar range (50); however so, it is possible that both the nicotinic and muscarinic macrophage acetylcholine receptor activities described here participate in the inhibition of macrophage TNF synthesis in vivo.

Figure 5:
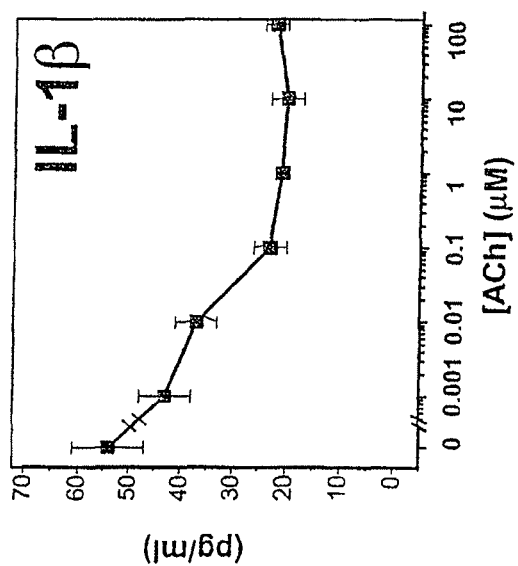
FIG. 5 is a graph summarizing experimental results showing that acetylcholine inhibits IL-1.beta. release from human macrophages in a dose-dependent manner.
Figure 6:
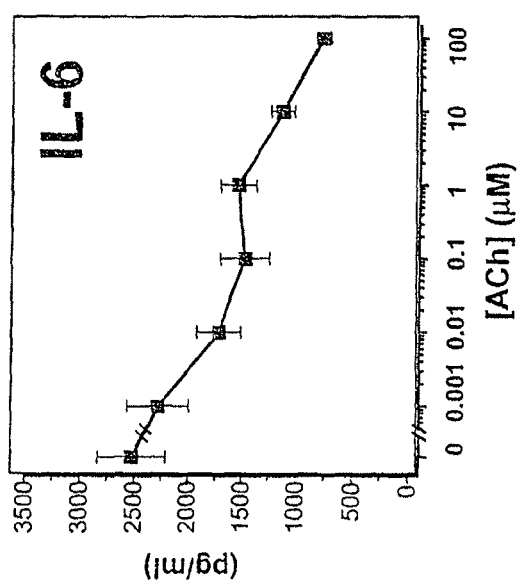
FIG. 6 is a graph summarizing experimental results showing that acetylcholine inhibits L-6 release from human macrophages in a dose-dependent manner.
Figure 7:
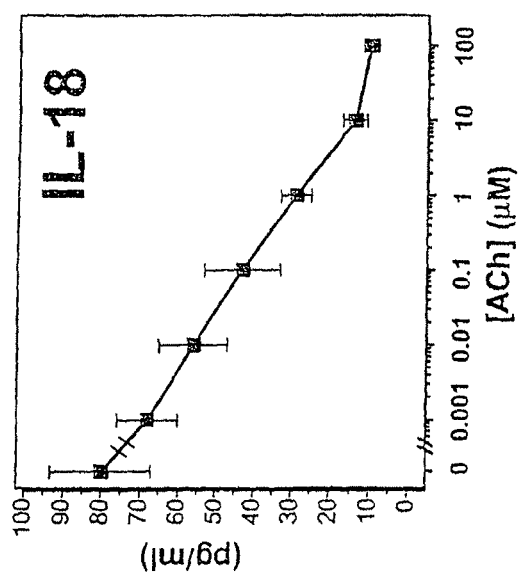
FIG. 7 is a graph summarizing experimental results showing that acetylcholine inhibits IL-18 release from human macrophages in a dose-dependent manner.
Figure 8:
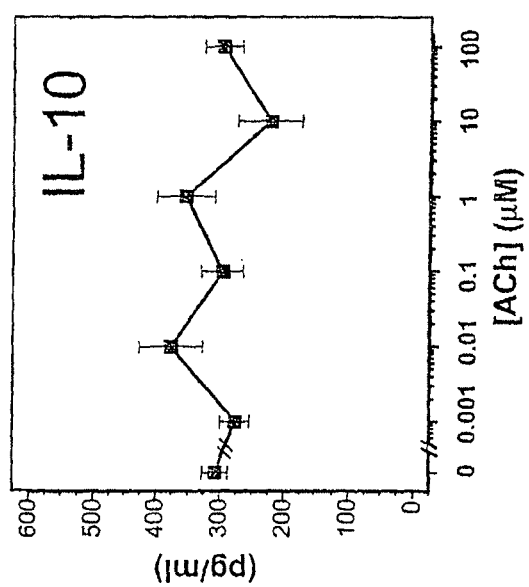
FIG. 8 is a graph summarizing experimental results showing that acetylcholine does not inhibit IL-10 release from human macrophages.

To assess specificity, the release of other macrophage-derived cytokines was measured in LPS-stimulated macrophage cultures treated with acetylcholine. In those experiments, human macrophage cultures were incubated with ACh at the indicated concentrations in the presence of pyridostigmine bromide (1 mM) and LPS (100 ng/ml) for 20 hours. IL-1.beta. (FIG. 5), IL-6 (FIG. 6) and IL-10 (FIG. 8) levels were measured in media using commercially available ELISA kits (R&D Systems Inc., Minneapolis, Minn.). IL-18 (FIG. 7) levels were determined by specific ELISA (Medical & Biological Laboratories Co., Ltd., Nagoya, Japan). Each sample was analyzed in triplicate. Data are expressed as Mean.+−.SEM from 4 separate experiments using macrophages prepared from 4 separate healthy donors. These experiments established that acetylcholine dose-dependently inhibits the release of other LPS-inducible cytokines (IL-1.beta., IL-6 and IL-18, FIGS. 5, 6, and 7, respectively), but does not prevent the constitutive release of the anti-inflammatory cytokine IL-10 (FIG. 8). Thus, acetylcholine specifically inhibits release of pro-inflammatory cytokines (FIGS. 5-7) by LPS-stimulated human macrophage cultures, but does not suppress release of the anti-inflammatory cytokine IL-10 (FIG. 8). Staining with tetrazolium salt MTT (3-(4,5-dimethylthiazol-2-yl)-2,5-diphenyl tetrazolium bromide, Sigma Chemical Co., St. Louis, Mo.), and Trypan blue exclusion of macrophage cultures treated with LPS and acetylcholine indicated that specific LPS-inducible cytokine inhibition was not due to cytotoxicity (not shown).

The molecular mechanism of acetylcholine inhibition of IL-1.beta. and IL-6 was investigated further by measuring gene-specific mRNA levels with biotin-labeled capture oligonucleotide probes in a calorimetric microplate assay (Quantikine mRNA, R&D Systems, Inc., Minneapolis, Minn.). Stimulation of human macrophage cultures with LPS for 2 hours significantly increased the mRNA levels of IL-1.beta. as compared to vehicle-treated controls (vehicle-treated IL-1.beta. mRNA=120.+−.54 attomole/ml vs LPS-stimulated IL-1.beta. mRNA=1974.+−.179 attomole/ml; n=3; P<0.01). Addition of acetylcholine in concentrations (100 nM) that significantly inhibited IL-1.beta. protein release did not significantly alter macrophage IL-1.beta. mRNA levels (acetylcholine-treated LPS-stimulated IL-1.beta. mRNA=2128.+−.65 attomole/ml; n=3). Similarly, LPS-stimulated IL-6 mRNA levels in macrophages were not significantly altered by acetylcholine concentrations that significantly inhibited IL-6 protein (LPS-stimulated IL-6 mRNA=1716.+−.157 attomole/ml vs. acetylcholine-treated LPS-stimulated IL-6 mRNA=1872.+−.91 attomole/ml; n=3). Together, these observations give evidence that acetylcholine post-transcriptionally inhibits the LPS-stimulated release of TNF, IL-1.beta. and IL-6 in macrophages.

The present results indicate that differentiated human macrophage cultures are extremely sensitive to acetylcholine and nicotine. Previous reports of cholinergic receptor activity in human peripheral blood mononuclear cells that were not differentiated into macrophages (53; 29; 46) suggested that maximal cholinergic responses required micromolar concentrations of cholinergic agonists. Our own studies establish that significantly higher concentrations of acetylcholine are required to suppress cytokine synthesis in differentiated human macrophages (acetylcholine E.C.$_{50}$ for inhibiting TNF=0.8.+−.0.2 mM, n=3). The pharmacological results now implicate an .alpha.-bungarotoxin-sensitive, nicotinic acetylcholine receptor activity that can modulate the macrophage cytokine response. This type of cholinergic receptor activity is similar to that previously described in peripheral blood mononuclear cells (53), except that macrophages are significantly more sensitive to cholinergic agonists as compared to peripheral blood mononuclear cells. The skilled artisan would not necessarily have expected macrophages to be so sensitive to cholinergic agonists, or even have any sensitivity at all, given what was previously known with mononuclear cells. Indeed, recent evidence in our lab has revealed nicotinic receptor subunit expression patterns in macrophages that are distinct from monocytes. Therefore, the skilled artisan would understand that molecular differences underlie the greater sensitivity to cholinergic agonists of macrophages over monocytes.

EXAMPLE 2

Inhibition of Endotoxic Shock by Stimulation of Efferent Vagus Nerve Fibers

To determine whether direct stimulation of efferent vagus nerve activity might suppress the systemic inflammatory response to endotoxin, adult male Lewis rats were subjected to bilateral cervical vagotomy, or a comparable sham surgical procedure in which the vagus nerve was isolated but not transected. Efferent vagus nerve activity was stimulated in vagotomized rats by application of constant voltage stimuli to the distal end of the divided vagus nerve 10 min before and again 10 min after the administration of a lethal LPS dose (15 mg/kg, i.v.). An animal model of endotoxic shock was utilized in these experiments. Adult male Lewis rats (280-300 g, Charles River Laboratories, Wilmington, Mass.) were housed at 22.degree. C. on a 12 h light/dark cycle. All animal experiments were performed in accordance with the National Institute of Health Guidelines under the protocols approved by the Institutional Animal Care and Use Committee of North Shore University Hospital/New York University School of Medicine. Rats were anesthetized with urethane (1 g/kg, intraperitoneally), and the trachea, the common carotid artery, and the jugular vein were cannulated with polyethylene tubing (Clay Adams, Parsippany, N.J.). The catheter implanted into the right common carotid artery was connected to a blood pressure transducer and an Acquisition System (MP 100, BIOPAC Systems, Inc., Santa Barbara, Calif.) for continuous registration of mean arterial blood pressure (MABP in FIG. 9). Animals were subjected to bilateral cervical vagotomy (VGX, n=7) alone or with electrical stimulation (VGX+STIM, n=7) or sham surgery (SHAM, n=7). In vagotomized animals, following a ventral cervical midline incision, both vagus trunks were exposed, ligated with a 4-0 silk suture, and divided. In sham-operated animals both vagal trunks were exposed and isolated from the surrounding tissue but not transected. Electrical stimulation of the vagus nerve was performed in animals previously subjected to vagotomy. In these groups, the distal end of right vagus nerve trunk was placed across bipolar platinum electrodes (Plastics One Inc., Roanoke, Va.) connected to a stimulation module (STM100A, Harvard Apparatus, Inc., Holliston, Miss.) as controlled by an Acquisition System (MP100, BIOPAC Systems, Inc., Santa Barbara, Calif.). Constant voltage stimuli (5 V, 2 ms, 1 Hz) were applied to the nerve for 20 min (10 min before LPS administration and 10 min after). Lipopolysaccharide (*Escherichia coli* 0111: B4; Sigma Chemical Co, St. Louis, Mo.; 10 mg/ml in saline) was sonicated for 30 minutes, and administered at a lethal dose (15 mg/kg, i.v.). Blood was collected from the right carotid artery 1 hour after LPS administration. Serum TNF levels were quantified by the L929 bioactivity assay. To determine liver TNF levels, animals were euthanized and livers rapidly excised, rinsed of blood, homogenized by polytron (Brinkman, Westbury, N.Y.) in homogenization buffer (PBS, containing 0.05% sodium azide, 0.5% Triton X-100 and a protease inhibitor cocktail (2 tablets/10 ml PBS, Boehringer Mannheim, Germany); pH 7.2; 4.degree. C.), and then sonicated for 10 minutes. Homogenates were centrifuged at 12,000 g for 10 minutes, and TNF levels in supernatants determined by ELISA (Biosource International, Camarillo, Calif.). Protein concentrations in the supernatants were measured by the Bio-Rad protein assay (Bio-Rad Lab., Hercules, Calif.), and liver TNF content normalized by the amount of protein in the sample. Blood samples were collected 1 hour after LPS and TNF was measured by L929 assay. *–P<0.05, **–P<0.005 vs. SHAM+LPS,#–P<0.05 vs. VGX+LPS.

Figure 9:
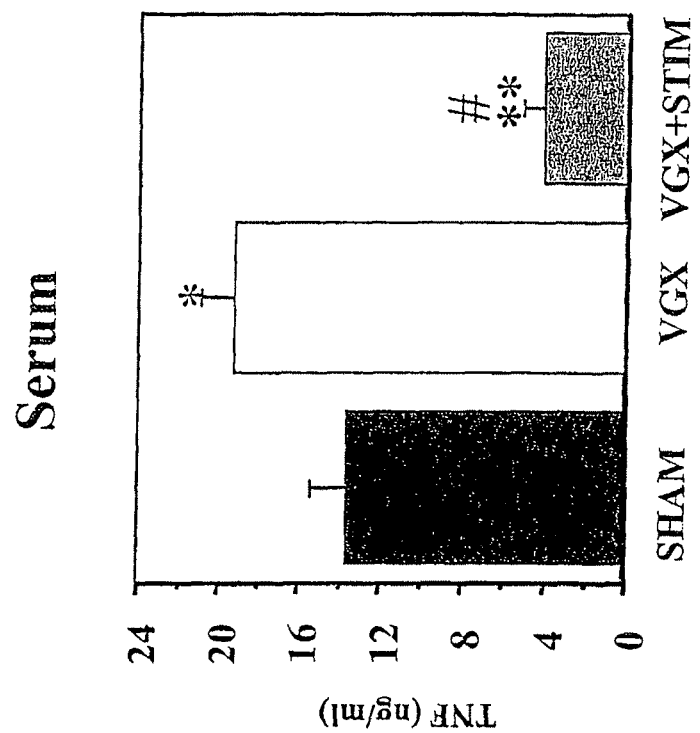
FIG. 9 is a graph summarizing experimental results showing that vagus nerve stimulation (STIM) after vagotomy (VGX) causes a decrease in circulating levels of TNF during endotoxemia induced by LPS.

As shown in FIG. 9, the results establish that electrical stimulation of the efferent vagus nerve significantly attenuates peak serum TNF levels; vagotomy without electrical stimulation significantly increased peak serum TNF levels as compared to sham-operated controls (P<0.05).

Figure 10:
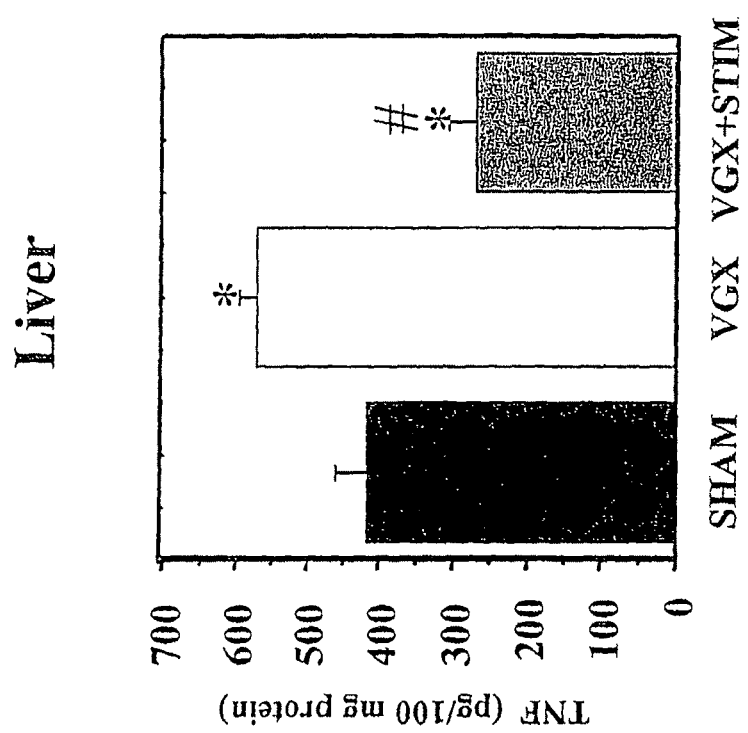
FIG. 10 is a graph summarizing experimental results showing that vagus nerve stimulation (STIM) after vagotomy (VGX) causes a decrease in levels of TNF in the liver during endotoxemia induced by LPS.

TNF levels in liver homogenates were measured next, because liver is a principle source of peak serum TNF during endotoxemia (26; 16). Electrical stimulation of the distal vagus nerve significantly attenuated hepatic TNF synthesis as compared to sham-operated controls (FIG. 10). In that figure, *–P<0.05 vs. SHAM+LPS,#–P<0.05 vs. VGX+LPS. These data directly implicate efferent vagus nerve signaling in the regulation of TNF production in vivo.

It was theoretically possible that electrical stimulation of the vagus nerve induced the release of humoral anti-inflammatory hormones or cytokines that inhibit TNF production. Measurements of corticosterone and IL-10 levels in sham-operated controls were performed (Table 1) to determine this.

In those studies, animals were subjected to either sham surgery (SHAM), vagotomy (VGX), or electrical stimulation with vagotomy (VGX+STIM) 30 minutes before systemic administration of LPS (15 mg/kg). Blood samples were collected 1 hour after administration of LPS or vehicle. Serum corticosterone was measured by radioimmunoassay (ICN Biomedicals, Costa Mesa, Calif.) and IL-10 was determined by ELISA (BioSource International, Camarillo, Calif.). All assays were performed in triplicate. The results are shown in Table 1, which indicates that endotoxemia was associated with increases in corticosterone and IL-10 levels. In agreement with previous studies, vagotomy significantly reduced corticosterone levels, in part because it eliminated the afferent vagus nerve signals to the brain that are required for a subsequent activation of the hypothalamic-pituitary-adrenal axis (14; 11). This decreased corticosteroid response and likely contributed to the increased levels of TNF observed in the serum and liver of vagotomized animals (FIGS. 9 and 10), because corticosteroids normally downregulate TNF production (41; 39). Direct electrical stimulation of the peripheral vagus nerve did not stimulate an increase in either the corticosteroid or the IL-10 responses. Thus, suppressed TNF synthesis in the serum and liver after vagus nerve stimulation could not be attributed to the activity of these humoral anti-inflammatory mediators.

TABLE 1 Effects of vagotomy and vagus nerve stimulation on serum IL-10 and corticosteroid levels during lethal endotoxemia. Group of animals IL-10 (ng/ml) Corticosterone (ng/ml) SHAM+vehicle N.D. 160.+–. 20 SHAM+LPS 8.+–.0.3 850.+–. 50 Vagotomy+LPS 9.+–0.0.4 570.+–.34*Vagotomy+LPS+Stimulation 9.+–.0.5 560.+–.43*

Data shown are Mean.+–.SEM, n=7 animals per group. *p<0.05 vs. SHAM+LPS.

Figure 11:
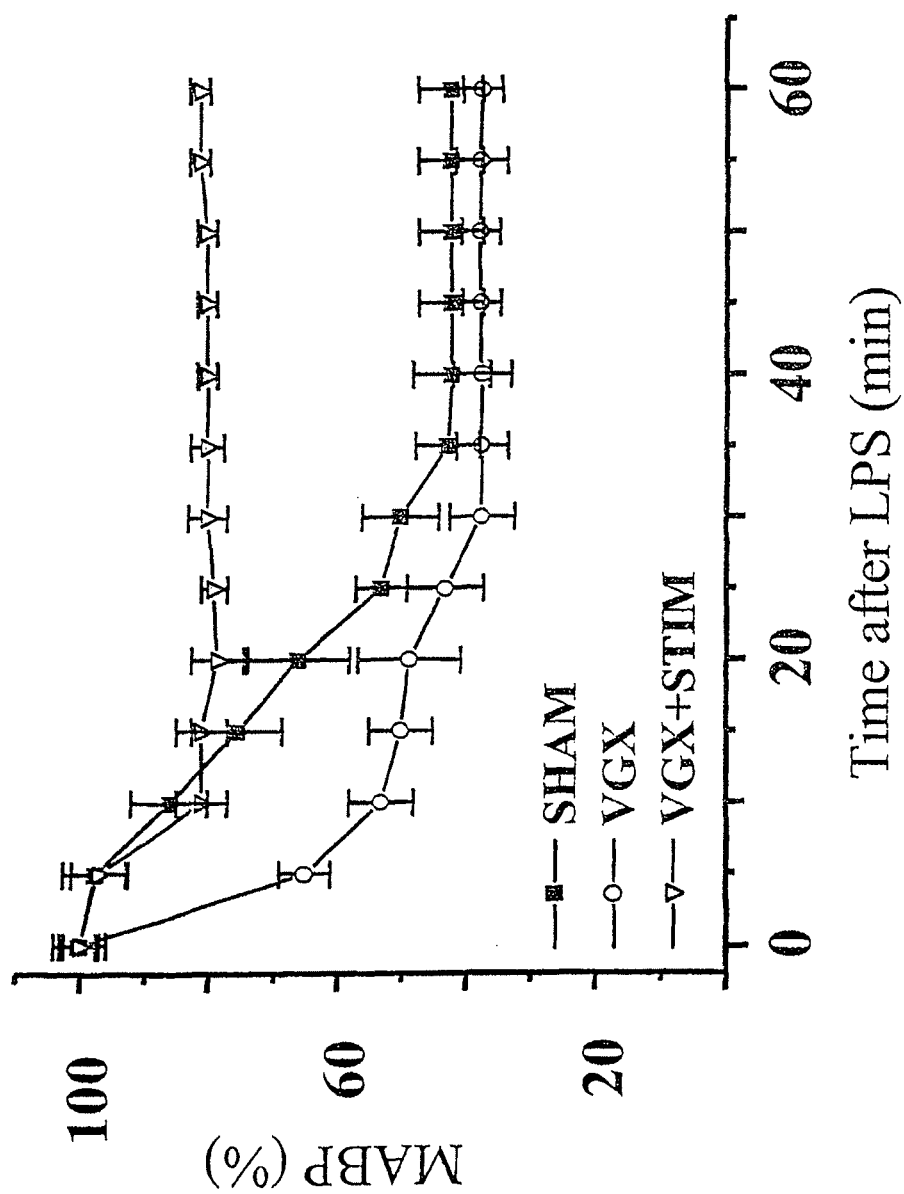
FIG. 11 is a graph summarizing experimental results showing that vagus nerve stimulation (STIM) after vagotomy (VGX) attenuates the development of hypotension (shock), as measured by mean arterial blood pressure (MABP), in rats exposed to lethal doses of endotoxin.

FIG. 11 shows the results of measurement of mean arterial blood pressure (MABP) in the same groups of animals as in FIGS. 9 and 10 (as described in methods). Circles—sham-operated rats (SHAM), triangles—vagotomized rats (VGX), squares—animals with electrical stimulation of the vagus nerve and vagotomy (VGX+STIM). LPS (15 mg/kg, i.v.) was injected at time=0. All data are expressed as % of MABP [MABP/MABP (at time=0).times.100%], Mean.+–.SEM; n=7. Sham-surgery, vagotomy and electrical stimulation with vagotomy did not significantly affect MABP in vehicle-treated controls (not shown).

Peripheral vagus nerve stimulation significantly attenuated the development of LPS-induced hypotension (shock) in rats exposed to lethal doses of endotoxin (FIG. 11). This observation was not unexpected, because TNF is a principle early mediator of acute endotoxin-induced shock (43-44). Vagotomy alone (without electrical stimulation) significantly shortened the time to development of shock as compared to sham-operated controls (sham time to 50% drop in mean arterial blood pressure 30.+–.3 minutes versus vagotomy time to 50% drop in mean arterial blood pressure=15.+–.2 minutes; P<0.05). This amplified development of shock following vagotomy alone corresponded to the decreased corticosteroid response and the increased TNF response.

Acetylcholine is a vasodilator that mediates nitric oxide-dependent relaxation of resistance blood vessels which causes a decrease in blood pressure. Thus, we wished to exclude the possibility that stimulation of the efferent vagus might have mediated a paradoxical hypertensive response. Hypertension was not observed following vagus nerve stimulation of controls given saline instead of endotoxin (not shown), indicating that protection against endotoxic shock by vagus nerve stimulation is specific. Considered together, these observations indicate that stimulation of efferent vagus nerve activity downregulates systemic TNF production and the development of shock during lethal endotoxemia.

EXAMPLE 3

Stimulation of Intact Vagus Nerve Attenuates Endotoxic Shock

Experiments were conducted to determine whether the inhibition of inflammatory cytokine cascades by efferent vagus nerve stimulation is effective by stimulation of an intact vagus nerve. Stimulation of left and right vagus nerves were also compared.

Figure 12:
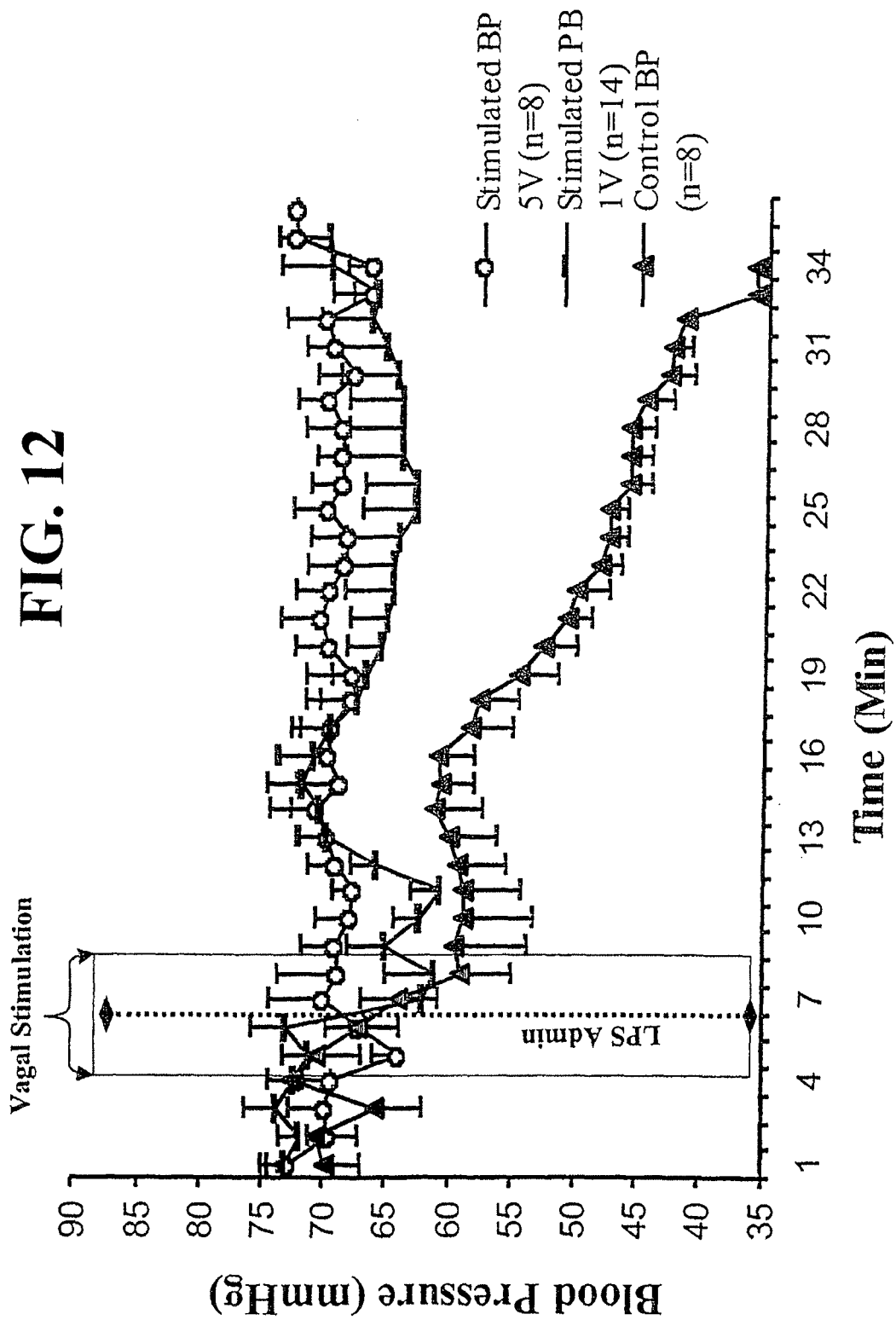
FIG. 12 is a graph summarizing experimental results showing that intact vagus nerve stimulation at 1V and 5V attenuates the development of shock in rats exposed to lethal doses of endotoxin.
Figure 13:
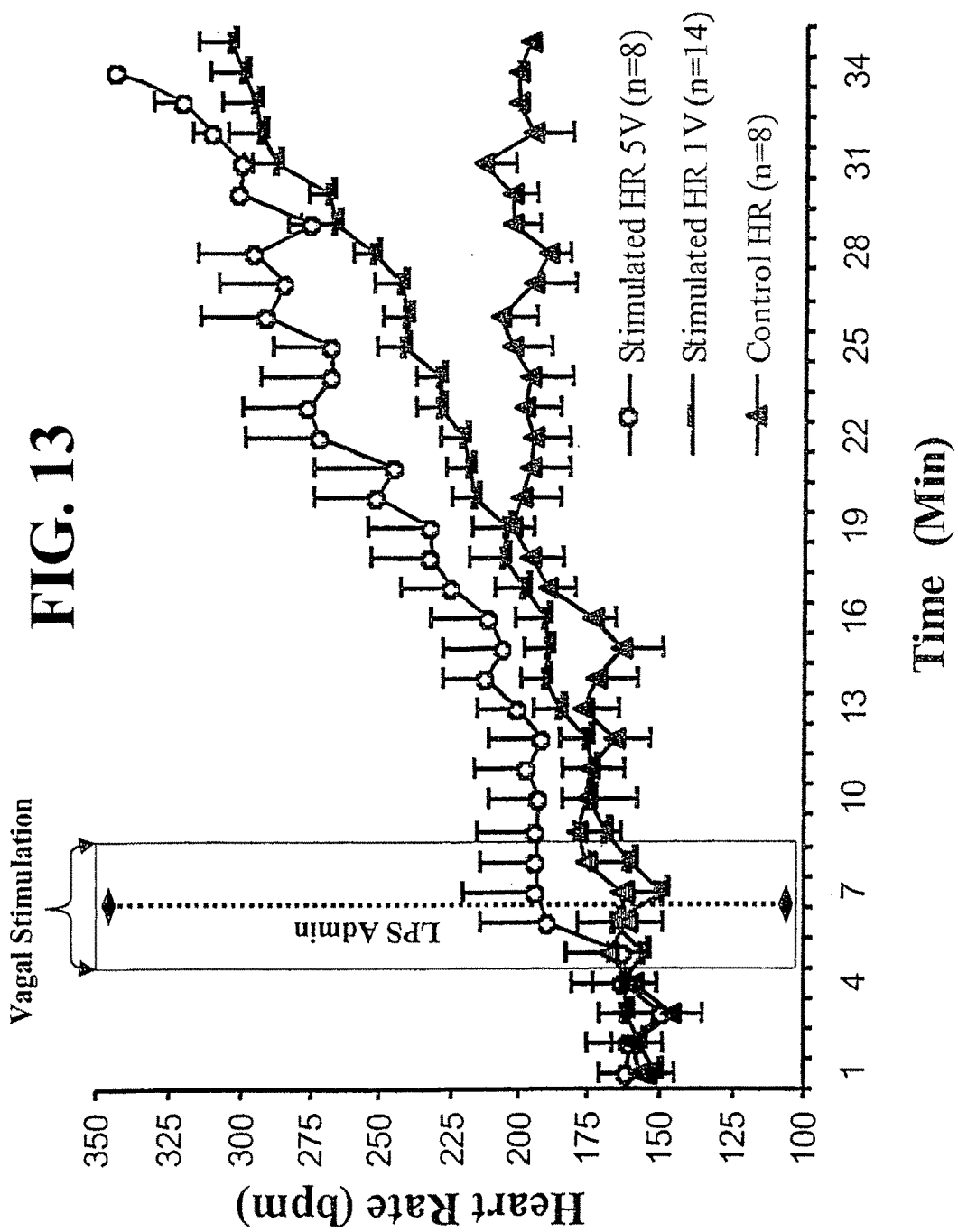
FIG. 13 is a graph summarizing experimental results showing that intact vagus nerve stimulation at 1V and 5V causes an increase in heart rate in rats exposed to lethal doses of endotoxin.
Figure 14:
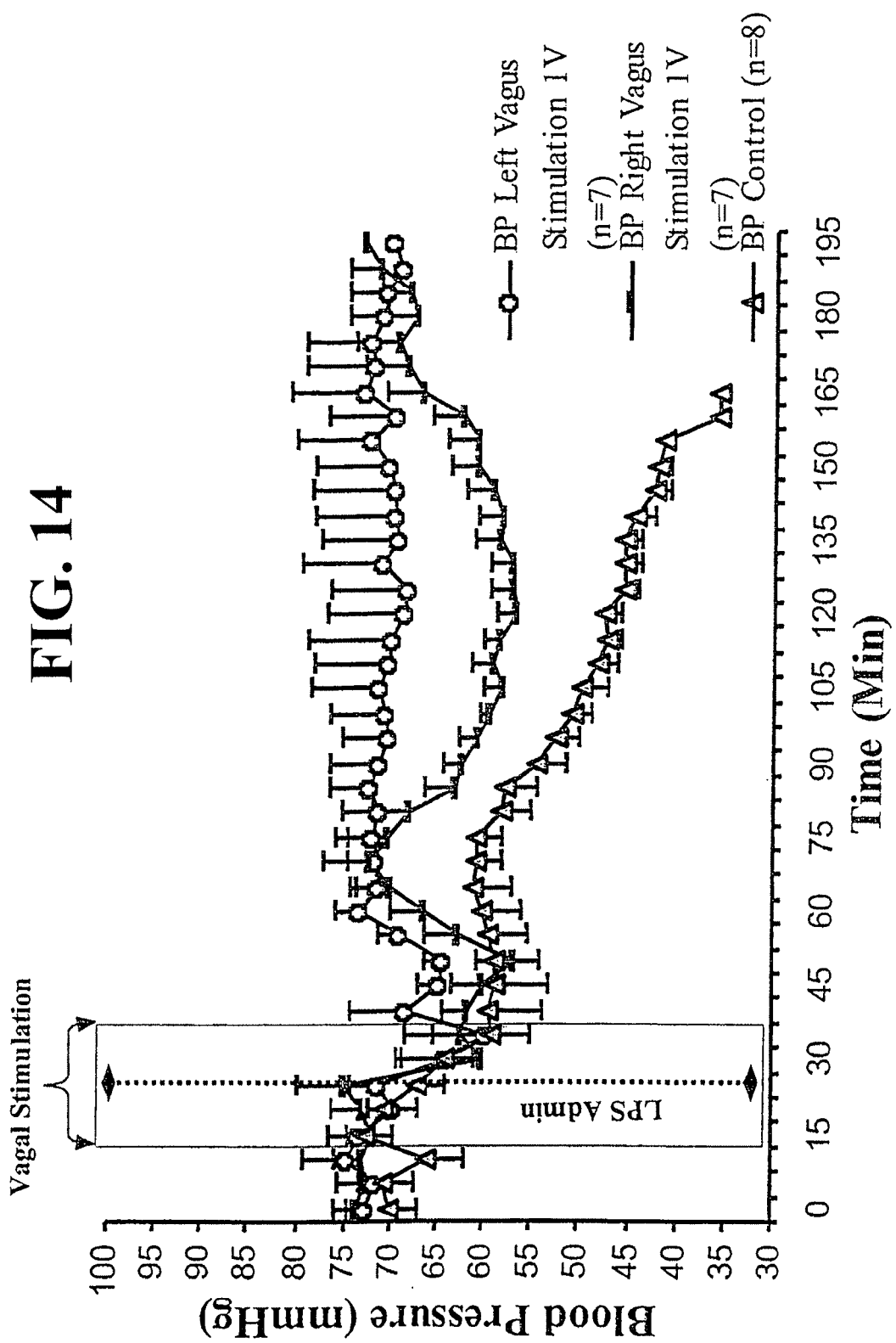
FIG. 14 is a graph summarizing experimental results showing that intact left vagus nerve stimulation at 1V stabilized blood pressure more effectively than intact right vagus nerve stimulation, in rats exposed to lethal doses of endotoxin.

The vagus nerves of anesthetized rats were exposed, and the left common iliac arteries were cannulated to monitor blood pressure and heart rate. Endotoxin (*E. coli* 0111:B4; Sigma) was administered at a lethal dose (60 mg/kg). In treated animals, either the left or the right intact vagus nerve was stimulated with constant voltage (5V or 1V, 2 ms, 1 Hz) for a total of 20 min., beginning 10 min. before and continuing 10 min. after LPS injection. Blood pressure and heart rate were through the use of a Bio-Pac M100 computer-assisted acquisition system. FIGS. 12-14 show the results of these experiments.

As shown in FIG. 12, within minutes after LPS injection, the blood pressure began to decline in both unstimulated rats and rats treated with a low dose (1V) of vagus nerve stimulation, while rats treated with a high dose (5V) of stimulation maintained more stable blood pressures. Between 30 and 40 min. post-LPS, the blood pressure stabilized in animals treated with a low dose of voltage.

FIG. 13 shows the heart rate of the experimental animals. Within minutes after LPS injection, the heart rate began to increase in rats stimulated with a high dose (5V) of vagus nerve stimulation. On the other hand, the heart rates of both unstimulated rats and rats stimulated with a low dose (1V) of voltage remained stable for approximately 60 min. post-LPS. After one hour, the heart rates of the rats treated with a low dose of stimulation began to increase, and reached levels comparable to those rats receiving a high dose of vagus nerve stimulation.

FIG. 14 compares left vs. right vagus nerve stimulation. Endotoxic animals were treated with 1V stimulation in either the left or the right vagus nerve. Within minutes after LPS injection, the blood pressure began to decline in all three stes of animals (unstimulated, left stimulation, right stimulation). Though both sets of stimulated animals recovered blood pressure, those animals receiving stimulation in the left vagus nerve maintained more stable blood pressures for the duration of the experiment. However, the difference in results between left and right vagus nerve stimulation was not statistically significant, and would not be expected to have any practical difference.

This set of experiments confirms that stimulation of an intact vagus nerve can effectively inhibit an inflammatory cytokine cascade sufficiently to alleviate conditions caused by the cascade.

EXAMPLE 4

Inhibition of HMG-1 Release from Macrophages by Nicotine

Experiments were performed to determine whether the inhibitory effect of cholinergic agonists on proinflammatory cytokines applied to HMG-1. Murine RAW 264.7 macrophage-like cells (American Type Culture Collection, Rockville, Md., USA) were grown in culture under DMEM supplemented with 10% fetal bovine serum and 1% glutamine. When the cells were 70-80% confluent, the medium was replaced by serum-free OPTI-MEM 1 medium. Nicotine (Sigma) was then added at 0, 0.1, 1, 10 or 100.mu.M. Five minutes after adding the nicotine, the cultures were treated with LPS (500 ng/ml). Culture medium was collected after 20 hr. The culture medium was concentrated with a Centricon T 10 filter, then analyzed by western blot, using an anti-HMG-1polyclonal antisera (WO 00/47104) and standard methods. Band densities were determined using a Bio-Rad Imaging densitometer.

Figure 15:
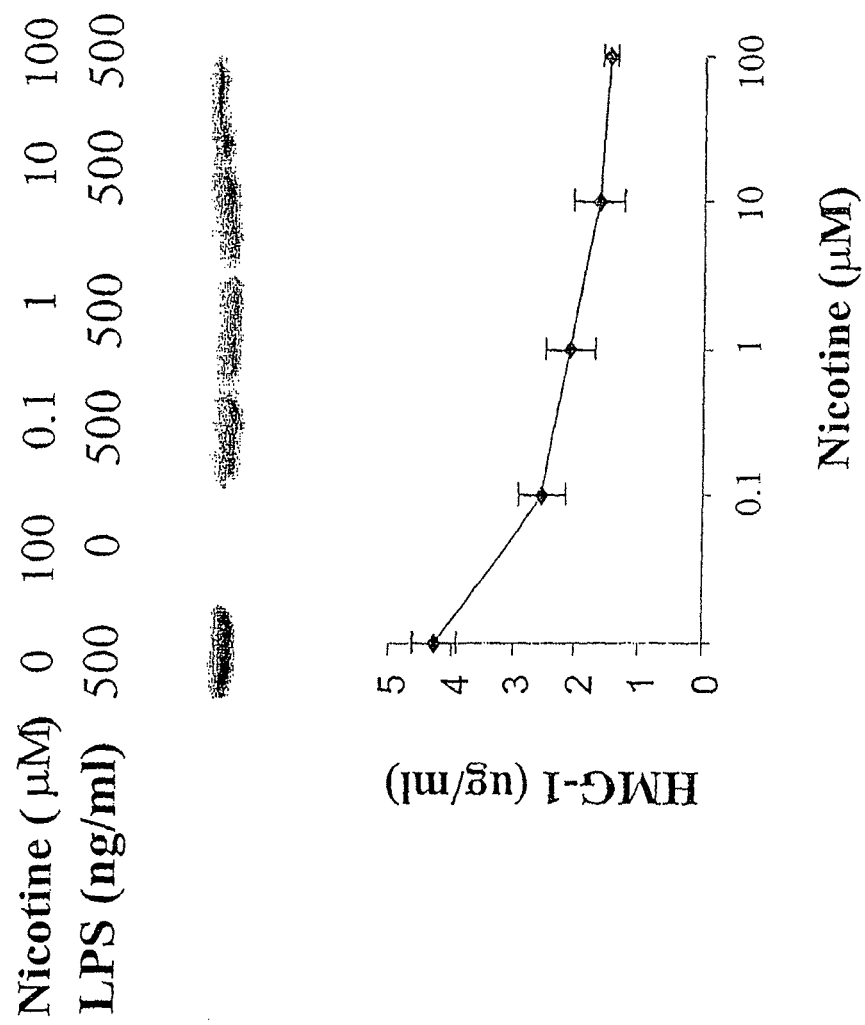
FIG. 15 is a western blot and graph of experimental results showing that addition of nicotine to RAW 264.7 macrophage-like cells inhibits the production of HMG-1 by the cells.

The results are shown in FIG. 15. The HMG-1 bands are shown along the top, with the corresponding nicotine and LPS concentrations, and the densities of the bands shown are graphed in the graph below. FIG. 15 clearly shows that nicotine inhibited HMG-1 production in a dose-dependent manner. This demonstrates that HMG-1 behaves as a proinflammatory cytokine in that its production can be inhibited by a cholinergic agonist.

The neural-immune interaction described here, which we term the "cholinergic anti-inflammatory pathway," can directly modulate the systemic response to pathogenic invasion. The observation that parasympathetic nervous system activity influences circulating TNF levels and the shock response to endotoxemia has widespread implications, because it represents a previously unrecognized, direct, and rapid endogenous mechanism that can be activated to suppress the lethal effects of biological toxins. The cholinergic anti-inflammatory pathway is positioned to function under much shorter response times as compared to the previously described humoral anti-inflammatory pathways. Moreover, activation of parasympathetic efferents during systemic stress, or the "flight or fight" response, confers an additional protective advantage to the host by restraining the magnitude of a potentially lethal peripheral immune response.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

EXAMPLE 5

Mechanical Vagus Nerve Stimulation is Sufficient to Inhibit Inflammatory Cytokine Release To determine the activation sensitivity of the cholinergic anti-inflammatory via VNS, the ability of mechanical nerve stimulation to activate the cholinergic anti-inflammatory pathway was examined. Male 8- to 12-week-old BALB/c mice (25-30 g; Taconic) were housed at 25.degree. C. on a 12 h light/dark cycle. Animals were allowed to acclimate to the facility for at least 7 days prior to experimental manipulation. Standard mouse chow and water were freely available. All animal experiments were performed in accordance with the National Institutes of Health (NIH) Guidelines under protocols approved by the Institutional Animal Care and Use Committee of the North Shore-Long Island Jewish Research Institute.

Mice were anesthetized with isoflurane (1.5-2.0%) and placed supine on the operating table. A ventral cervical midline incision was used to expose and isolate the left cervical vagus nerve. The left vagus nerve was exposed via a midline cervical incision. After isolating the nerve from the surrounding structures, the surgery was terminated, without subsequent electrode placement. LPS administration preceded surgery by 5 min. Sham operated mechanical VNS mice underwent cervical incision followed by dissection of the underlying submandibular salivary glands only. The vagus nerve was neither exposed nor isolated.

Mice were injected with endotoxin (*Escherichia coli* LPS 0111:B4; Sigma) that was dissolved in sterile, pyrogen-free saline at stock concentrations of 1 mg/ml. LPS solutions were sonicated for 30 min immediately before use for each experiment. Mice received an $LD_{50}$ dose of LPS (7.5 mg/kg, i.p.). Blood was collected 2 h after LPS administration, allowed to clot for 2 h at room temperature, and then centrifuged for 15 min at 2,000.times.g. Serum samples were stored at −20.degree. C. before analysis. TNF concentrations in mouse serum were measured by ELISA (R & D Systems).

Figure 16:
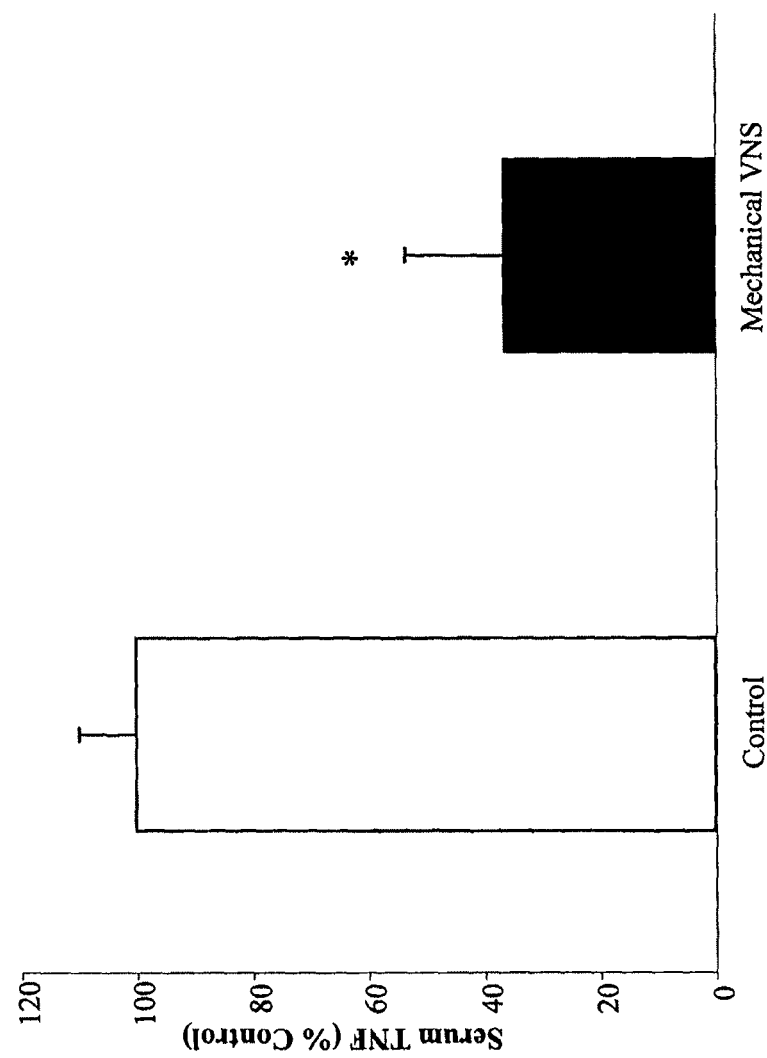
FIG. 16 is a bar graph showing the percentage of TNF in the serum of mice injected with endotoxin and treated with mechanical stimulation of the vagus nerve compared with untreated controls.

Mechanical VNS significantly reduced TNF production during lethal endotoxemia (FIG. 16). Compared with the control group, the mechanical VNS group had a 75.8% suppression in TNF production (control=1819.+−.181 pg/ml vs. mechanical VNS=440.+−.64 pg/ml, p=0.00003). These results indicate that mechanical nerve stimulation is sufficient to inhibit cytokine release.

EXAMPLE 6

Non-Invasive External Cervical Massage is Sufficient to Activate the Cholinergic Anti-Inflammatory Pathway To determine whether mechanical VNS could be utilized in a non-invasive, transcutaneous manner to elicit anti-inflammatory effects, a model of murine cervical massage in lethal endotoxemia was developed. Mice were anesthetized and positioned as described above. Following the midline cervical incision, a unilateral left total submandibular sialoadenectomy was performed. No further dissection was performed, and the underlying vagus nerve was not exposed. Following closure of the incision, animals received external vagus nerve cervical massage using a cotton-tip applicator. Cervical massage was performed using alternating direct pressure applied antero-posteriorly adjacent to the left lateral border of the trachea. Each pressure application was defined as one stimulation. The number of stimulations was quantified by frequency and time. The lowest dose cervical massage group underwent 40 sec stimulation at 0.5 stimulations s.sup.-1. The middle dose cervical massage group underwent 2 min stimulation at 1 stimulations s.sup.-1. The highest dose cervical massage group underwent 5 min stimulation at 2 stimulations s.sup.-1. Sham operated cervical massage mice underwent unilateral left submandibular sialoadenectomy only.

Figure 17:
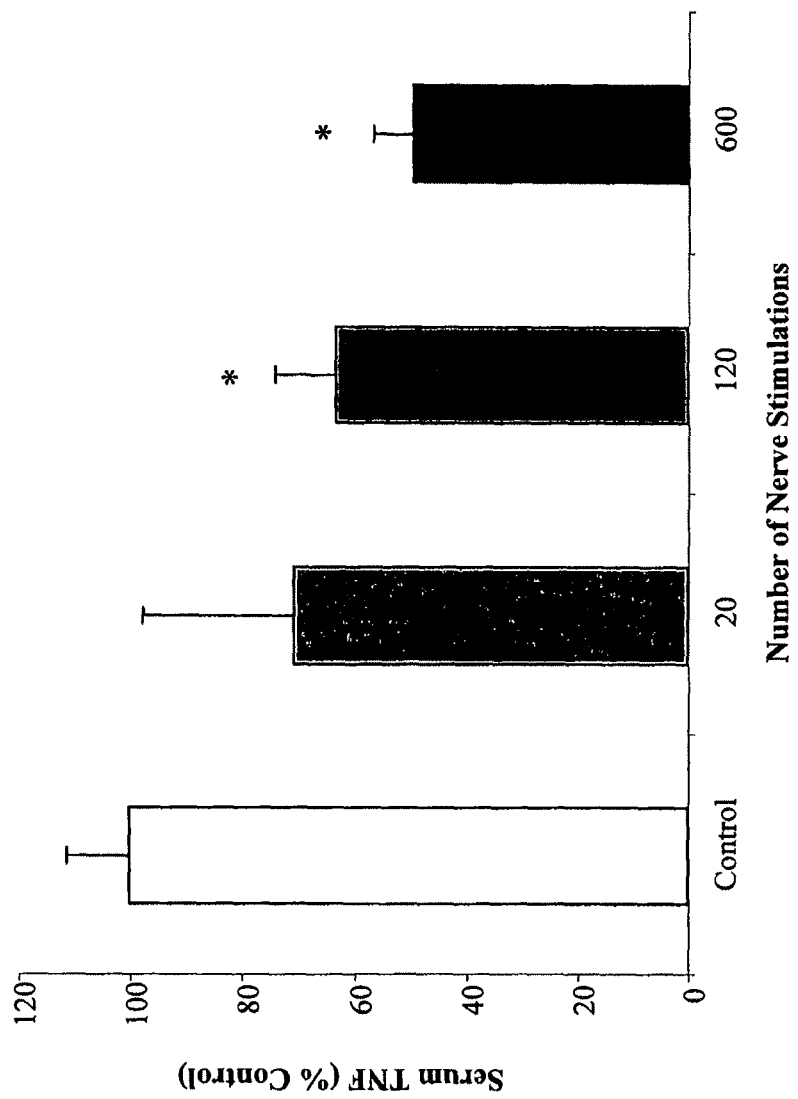
FIG. 17 is a dose response curve for TNF suppression in mice injected with enodoxin. The y axis is the percentage of TNF in the serum relative to untreated control; and the x axis is the number of vagus nerve stimulations quantified by frequency and time.

A dose response curve for TNF suppression was generated from these stimulation groups and is shown in FIG. 17. The 40 sec (0.5 Hz) group had a 29.2% suppression of TNF (control=1879.+-.298 pg/ml vs. massage=1331.+-.503 pg/ml, p=0.38). The 2 min (1 Hz) group had a 36.8% suppression of TNF (control=1909.+-.204 pg/ml vs. massage=1206.+-.204 pg/ml, p=0.04). The 5 min (2 Hz) group had a 50.7% suppression of TNF (control=2749.+-.394 pg/ml vs. massage=1355.+-.152 pg/ml, p=0.02). These data indicate that a non-invasive, easily performed, low risk, accepted clinical therapeutic maneuver could be utilized to significantly reduce systemic inflammation.

REFERENCES CITED

1. Antonica, A., et al., J. Auton. Nerv. Syst., 48:187-97, 1994.
2. Besedovsky, H., et al., Science, 233:652-54, 1986.
3. Blackwell, T. S., and Christman, J. W., Br. J. Anaesth., 77: 110-17, 1996.
4. Blum, A. and Miller, H., Am. Heart J., 135:181-86, 1998.
5. Borovikova, L. V., et al., Nature, 405: 458-62, 2000a.
6. Borovikova, L. V., et al., Auton. Neurosci., 20:141-47, 2000b.
7. Bumgardner, G. L., and Orosz, C. G., Semin. Liver Dis., 19: 189-204, 1999.
8. Carteron, N. L., Mol. Med. Today, 6:315-23, 2000.
9. Dibbs, Z., et al., Proc. Assoc. Am. Physicians, 111:423-28, 1999.
10. Dinarello, C. A., FASEB J., 8:1314-25, 1994.
11. Fleshner, M., et al., J. Neuroimmunol., 86:134-41, 1998.
12. Fox, D. A., Arch. Intern. Med., 28:437-444, 2000.
13. Gattorno, M., et al., J. Rheumatol., 27:2251-2255, 2000.
14. Gaykema, R. P., et al., Endocrinology, 136:4717-4720, 1995.
15. Gracie, J. A., et al., J. Clin. Invest., 104:1393-1401, 1999.
16. Gregory, S. H. and Wing, E. J., Immunology Today, 19:507-10, 1998.
17. Guslandi, M., Br. J. Clin. Pharmacol., 48:481-84, 1999.
18. Hirano, T., J. Surg. Res., 81: 224-29, 1999.
19. Hommes, D. W. and van Deventer, S. J., Curr. Opin. Clin. Nutr. Metab. Care, 3:191-95, 2000.
20. Hsu, H. Y., et al., J. Pediatr. Gastroenterol., 29:540-45, 1999.
21. Hu, X. X., et al., J. Neuroimmunol., 31:35-42, 1991.
22. Jander, S. and Stoll, G., J. Neuroimmunol., 114:253-58, 2001.
23. Kanai, T. et al., Digestion, 63 Suppl. 1:37-42, 2001.
24. Katagiri, M., et al., J. Clin, Gastroenterol., 25 Suppl. 1: S211-14, 1997.
25. Kimmings, A. N., et al., Eur. J. Surg., 166:700-05, 2000.
26. Kumins, N. H., et al., SHOCK, 5:385-88, 1996.
27. Lee, H. G., et al., Clin. Exp. Immunol., 100:139-44, 1995.
28. Lipton, J. M. and Catania, A., Immunol. Today, 18:140-45, 1997.
29. Madretsma, G. S., et al., Immunopharmacology, 35:47-51, 1996.
30. McGuinness, P. H., et al., Gut, 46:260-69, 2000.
31. Nathan, C. F., J. Clin. Invest., 79:319-26, 1987.
32. Pulkki, K. J., Ann. Med., 29:339-43, 1997.
33. Prystowsky, J. B. and Rege, R. V., J. Surg. Res., 71; 123-26 1997.
34. Rayner, S. A. et al., Clin. Exp. Immunol., 122:109-16, 2000.
35. Romanovsky, A. A., et al., Am. J. Physiol., 273:R407-13, 1997.
36. Sandborn, W. J., et al., Ann. Intern. Med, 126:364-71, 1997.
37. Sato, E., et al., Am. J. Physiol., 274:L970-79, 1998.
38. Sato, K. Z., et al., Neurosci. Lett., 266:17-20, 1999.
39. Scheinman, R. I., et al., Science, 270:283-86, 1995.
40. Sher, M. E., et al., Inflamm. Bowel Dis., 5:73-78, 1999.
41. Sternberg, E. M., J. Clin. Invest., 100:2641-47, 1997.
42. Thompson, A., Ed. The Cytokine Handbook, 3.sup.rd ed., Academic Press, 1998.
43. Tracey, K. J. et al., Nature, 330:662-64, 1987.
44. Tracey, K. J. et al., Science, 234:470-74, 1986.
45. Tsutsui, H., et al., Immunol. Rev., 174:192-209, 2000.
46. van Dijk, A. P., et al., Eur. J. Clin. Invest., 28:664-71, 1998.
47. Wang, H., et al., Science, 285:248-51, 1999.
48. Waserman, S., et al., Can. Respir. J., 7:229-37, 2000.
49. Watanabe, H. et al., J. Reconstr. Microsurg., 13:193-97, 1997.
50. Wathey, J. C., et al., Biophys. J., 27:145-64, 1979.
51. Watkins, L. R. and Maier, S. F., Proc. Natl. Acad. Sci. U.S.A., 96:7710-13, 1999.
52. Watkins L. R., et al., Neurosci. Lett. 183:27-31, 1995.
53. Whaley, K., et al., Nature, 293:580-83, 1981.
54. Woiciechowsky, C., et al., Nat. Med., 4: 808-13, 1998.
55. Yeh, S. S., and Schuster, M. W., Am. J. Clin. Nutr., 70, 183-97, 1999.
56. Zhang and Tracey, in The Cytokine Handbook, 3.sup.rd ed., Ed. Thompson, Academic Press, 515-47, 1998.
57. PCT patent publication WO 00/47104.
58. Sambrook, et al., Molecular Cloning: A Laboratory Manual, Cold Spring Harbor Laboratory Press, 1989.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A method for treating inflammation by inhibiting an inflammatory cytokine cascade in a patient, wherein the method comprises:

evoking a sustained inhibition of the patient's inflammatory cytokine cascade by electrically stimulating the patient's vagus nerve for a first duration, followed by a second duration during which the patient's vagus nerve is not electrically stimulated, wherein the second duration is at least three times longer than the first duration, wherein at the end of the second duration the levels of inflammatory cytokines are inhibited by at least 20% over the untreated state, and wherein the patient's heart rate remains stable for 10 minutes after the vagus nerve is electrically stimulated.

2. The method of claim 1, wherein the first duration is less than about 20 min.

3. The method of claim 1, wherein the second duration is greater than about 30 min.

4. The method of claim 1, wherein the patient's vagus nerve is stimulated in an amount sufficient to inhibit the inflammatory cytokine cascade without stimulating humoral anti-inflammatory mediators.

5. The method of claim 1, wherein the electrical stimulation of the patient's vagus nerve does not stimulate a corticosteroid or IL-I0 response.

6. The method of claim 1, further comprising electrically stimulating the patient's entire vagus nerve, including afferent and efferent nerves.

7. The method of claim 1, further comprising electrically stimulating the patient's efferent vagus nerve by stimulating close to the target organ served by the efferent fibers or by directly stimulating the target organ.

8. A method of inhibiting an inflammatory cytokine cascade of a patient, wherein the method comprises:
    evoking a sustained inhibition of the patient's inflammatory cytokine cascade by electrically stimulating the patient's vagus nerve for a first duration of 20 minutes or less, followed by a second duration during which the patient's vagus nerve is not electrically stimulated, wherein the second duration is at least three times longer than the first duration,
    wherein at the end of the second duration the levels of inflammatory cytokines are inhibited by at least 20% over the untreated state, and wherein the patient's heart rate remains stable for 10 minutes after the vagus nerve is electrically stimulated.

9. The method of claim 8, wherein the second duration is greater than about 30 min.

10. The method of claim 8, wherein the patient's vagus nerve is stimulated in an amount sufficient to inhibit the inflammatory cytokine cascade without stimulating humoral anti-inflammatory mediators.

11. The method of claim 8, wherein the electrical stimulation of the patient's vagus nerve does not stimulate a corticosteroid or IL-I0 response.

12. The method of claim 8, further comprising electrically stimulating the patient's entire vagus nerve, including afferent and efferent nerves.

13. The method of claim 8, further comprising electrically stimulating the patient's efferent vagus nerve by stimulating close to the target organ served by the efferent fibers or by directly stimulating the target organ.

14. A method of providing therapy to a patient suffering from a condition that causes an inflammatory cytokine cascade, the method comprising:
    electrically stimulating vagus nerve activity in an amount sufficient to induce sufficient secretion of a cholinergic agonist to inhibit the inflammatory cytokine cascade by at least 20% over the untreated state, wherein the patient's heart rate remains stable for 10 minutes after the vagus nerve is electrically stimulated; and
    monitoring a marker of the patient's inflammatory cytokine cascade.

15. The method of claim 14, the stimulating step further comprising stimulating vagus nerve activity in an amount sufficient to induce secretion of acetylcholine.

16. The method of claim 14, wherein the patient's vagus nerve is stimulated in an amount sufficient to inhibit the inflammatory cytokine cascade without stimulating humoral anti-inflammatory mediators.

17. The method of claim 14, wherein the electrical stimulation of the patient's vagus nerve does not stimulate a corticosteroid or IL-I0 response.

18. The method of claim 14, wherein electrically stimulating vagus nerve activity comprises electrically stimulating the patient's entire vagus nerve, including afferent and efferent nerves.

19. The method of claim 14, wherein electrically stimulating vagus nerve activity comprises electrically stimulating the patient's efferent vagus nerve by stimulating close to the target organ served by the efferent fibers or by directly stimulating the target organ.

20. The method of claim 1, further comprising measuring a level of an inflammatory cytokine both before and after the step of electrically stimulating the patient's vagus nerve.

* * * * *